United States Patent
Wei et al.

(10) Patent No.: US 12,421,238 B2
(45) Date of Patent: Sep. 23, 2025

(54) SELECTIVE DIHYDROPYRROLOPYRIMIDINE JAK2 INHIBITORS

(71) Applicant: CHENGDU JINRUI FOUNDATION BIOTECH CO., LTD., Chengdu (CN)

(72) Inventors: Nongnong Wei, Shanghai (CN); Hua Jin, Shanghai (CN); Yongyong Zheng, Shanghai (CN); Feng Zhou, Shanghai (CN); Meihua Huang, Shanghai (CN)

(73) Assignee: CHENGDU JINRUI FOUNDATION BIOTECH CO., LTD., Chengdu (CN)

( * ) Notice: Subject to any disclaimer, the term of this patent is extended or adjusted under 35 U.S.C. 154(b) by 918 days.

(21) Appl. No.: 17/581,178

(22) Filed: Jan. 21, 2022

(65) Prior Publication Data

US 2022/0144844 A1    May 12, 2022

Related U.S. Application Data

(63) Continuation of application No. PCT/CN2019/127676, filed on Dec. 23, 2019.

(30) Foreign Application Priority Data

Jul. 30, 2019    (CN) .......................... 201910698079.2

(51) Int. Cl.
C07D 487/04    (2006.01)
(52) U.S. Cl.
CPC .................. C07D 487/04 (2013.01)
(58) Field of Classification Search
CPC .................................................... C07D 487/04
See application file for complete search history.

(56) References Cited

U.S. PATENT DOCUMENTS

2016/0222014 A1*    8/2016    Venkatesan .......... A61K 31/538

FOREIGN PATENT DOCUMENTS

| WO | 2007140222 A2 | 12/2007 |
| WO | 2009098236 A1 | 8/2009 |
| WO | 2015038417 A1 | 3/2015 |
| WO | 2018098561 A1 | 6/2018 |

OTHER PUBLICATIONS

International Search Report and Written Opinion, China Patent Office, Application No. PCT/CN2019/127676, mailed May 6, 2020, 5 pages.

* cited by examiner

*Primary Examiner* — Adam C Milligan
*Assistant Examiner* — Karen Cheng
(74) *Attorney, Agent, or Firm* — Scully, Scott, Murphy & Presser, P.C.

(57) ABSTRACT

The present invention relates to the technical field of biomedicine, particularly to a selective dihydropyrrolopyrimidine JAK2 inhibitor or a pharmaceutically acceptable salt thereof. Compared with the prior art, the pyrrolopyrimidine compounds, stereoisomers and pharmaceutically acceptable salts thereof provided by the present invention exhibit better inhibitory activity for Janus Kinase and significantly better selectivity for JAK2 inhibitory targets. In addition, the preferred compounds of the present invention exhibit good pharmacokinetic properties and have the potential to be developed as selective JAK2 inhibitors.

12 Claims, No Drawings

SELECTIVE DIHYDROPYRROLOPYRIMIDINE JAK2 INHIBITORS

CROSS-REFERENCE TO RELATED APPLICATIONS

The present application is a continuation application of PCT application No. PCT/CN2019/127676, filed on Dec. 23, 2019, which is hereby incorporated by reference in its entirety.

TECHNICAL FIELD

The present invention relates to the technical field of biomedicine, particularly to a selective dihydropyrrolopyrimidine JAK2 inhibitor or a pharmaceutically acceptable salt thereof.

BACKGROUND ART

JAK (i.e., Janus Kinase) is a non-receptor type tyrosine protein kinase (PTK). The JAK-STAT pathway is mainly composed of four parts: (1) an extracellular signal factor; (2) a receptor; (3) a JAK kinase; and (4) a signal transducer and activator of transcription (STAT). JAK-STAT is the most important signal pathway besides the second messenger system. JAK senses extracellular signals by binding to receptors (such as interferons, interleukins and growth factors) and transmits information to STATs. Phosphorylated STATs can be transferred from the cell to the nucleus. Each different STAT binds to a different promoter DNA sequence. Promoters control the expression of their DNA sequences, causing changes in DNA transcription and activity levels, which in turn affect basic cell functions such as cell growth, differentiation, and death.

The JAK family proteins include 4 members, including JAK1, JAK2, JAK3, and TYK2. From the viewpoint of gain-of-function expression or mutation analysis, JAK1 and JAK3 are more related to immune regulation, while JAK2 is directly related to the production of red blood cells and platelets. From the viewpoint of loss of function analysis, although JAK1 and JAK2 functional loss-related diseases have not been found in humans, the loss of function of JAK1 and JAK2 can cause the death of mouse embryos, which may indirectly indicate the importance of the physiological functions of JAK1/2. The loss of function of JAK3 can cause serious comprehensive immune deficiency, which is the basis for targeting JAK3 to regulate autoimmune-related diseases as mentioned below. There are few studies on the function of TYK2, and it has been reported that it can cause deficiencies related to intrinsic immunity.

The discovery of JAK2 V617F myeloproliferative neoplasm (MPN) has greatly promoted the development of JAK2 inhibitors. MPN is a group of chronic diseases characterized by the proliferation of abnormal hematopoietic progenitor cells in the bone marrow. MPN includes myelofibrosis (MF), polycythemia vera (PV), essential thrombocythemia (ET) and chronic myelogenous leukemia (CML). Approximately 95% of PV patients and 50-60% of MF and ET patients have been found to have JAK2 V617F single amino acid mutation, which causes a conformational change of JAK2, resulting in the continuous activation of the kinase region that does not depend on extracellular cytokine signals. It in turn causes cell proliferation and blood cancer.

Ruxolitinib reported in WO2007070514A was originally developed by Incyte and is a small molecule JAK1/JAK2 inhibitor. Ruxolitinib was approved by the FDA in November 2011 for the treatment of medium and high-risk MF. Ruxolitinib was further approved in 2014 for the treatment of polycythemia vera. Ruxolitinib can alleviate the enlargement of the spleen caused by the JAK2 V617F mutation and reduce the asthenia in patients.

Ruxolitinib cannot reduce the JAK2V617F mutation load of mutant blood cancer cells, so Ruxolitinib can hardly bring about a curative effect. In addition, the selectivity of Ruxolitinib to the JAK2 target is not high, and the side effects are obvious. The side effects of Ruxolitinib mainly include anemia, thrombocytopenia, neutropenia, diarrhea, etc.

Early reports showed that after Ruxolitinib was discontinued, there was an obvious and poor prognosis inflammatory syndrome. In the following 3 years of follow-up, no sustained similar adverse reactions were observed, suggesting that such reactions may be severe withdrawal inflammatory syndrome caused by discontinuation of Ruxolitinib. The size of the spleen should be closely monitored. If the spleen still grows during Ruxolitinib treatment, the related symptoms of MF may return to the baseline level or even continue to progress after stopping the drug. Therefore, when considering interrupting Ruxolitinib treatment, the dose should be gradually reduced or corticosteroids should be used in combination.

The development of new generation of MPN medicaments focuses on selective inhibitors of JAK2, which is expected to reduce the excessive side effects caused by targeting JAK1 while increasing the efficacy.

So far, JAK inhibitors have been disclosed in many patent applications, such as CN101370792A, WO2010017122, CN101421250A, WO2010074947A1, etc. Although a variety of JAK inhibitors have been disclosed, there is still a need to develop new JAK inhibitor compounds with better efficacy and lower side effects, especially selective JAK2 inhibitors.

SUMMARY OF THE INVENTION

To overcome the technical problems existing in the prior art, the objective of the present invention is to provide a selective dihydropyrrolopyrimidine JAK2 inhibitor.

To achieve the above objective and other related objectives, the present invention provides a selective dihydropyrrolopyrimidine JAK2 inhibitor of formula I or a pharmaceutically acceptable salt thereof:

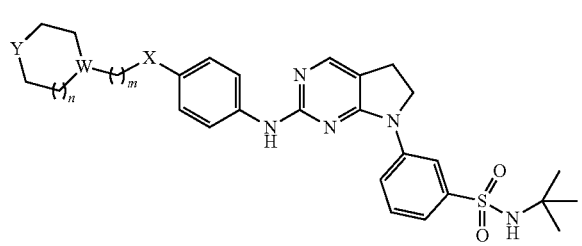

wherein
X is O or does not exist;
Y is O, S, $SO_2$ or NR;
W is N or CH;
R is hydrogen, $C_{1-6}$ alkyl, $C_{2-6}$ alkenyl, $C_{2-6}$ alkynyl, $C_{1-6}$ alkoxy or $C_{1-6}$ carbonyl;
m is 0, 1, 2, 3, 4, 5 or 6; and n is 0, 1 or 2.
Preferably,
X is O or does not exist;
Y is O, S, SO$_2$ or NR;
W is N or CH;
R is hydrogen or C$_{1-4}$ alkyl;
m is 0, 1, 2 or 3; and
n is 0 or 1.
More preferably,
X is O or does not exist;
Y is O, S, SO$_2$ or NR;
W is N or CH;

R is hydrogen or C$_{1-3}$ alkyl;
m is 0, 1 or 2; and
n is 0 or 1.
Further,
X is O or does not exist;
Y is O, S, SO$_2$ or NR;
W is N or CH;
R is hydrogen or methyl;
m is 0, 1 or 2; and
n is 0 or 1.

Typical compounds of the present invention include but are not limited to the following compounds in Table 1:

Table 1

| Compound | Structural formula |
| --- | --- |
| I-1 | 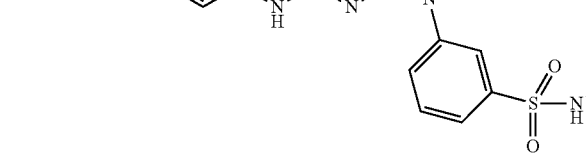 |
| I-2 | 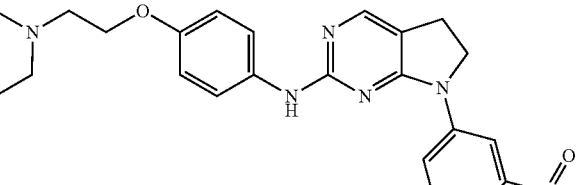 |
| I-3 | 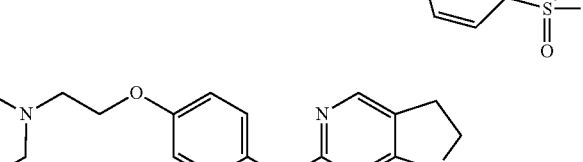 |
| I-4 | 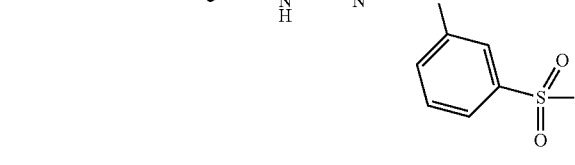 |
| I-5 | 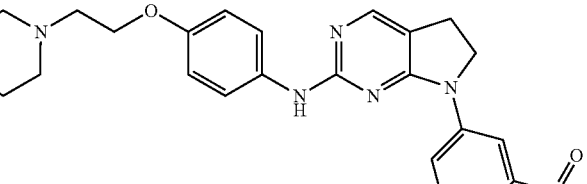 |

Table 1-continued

| Compound | Structural formula |
|---|---|
| I-6 | |
| I-7 | |
| I-8 | |
| I-9 | |
| I-10 | |
| I-11 | |

Table 1-continued
| Compound | Structural formula |
|---|---|
| I-12 | 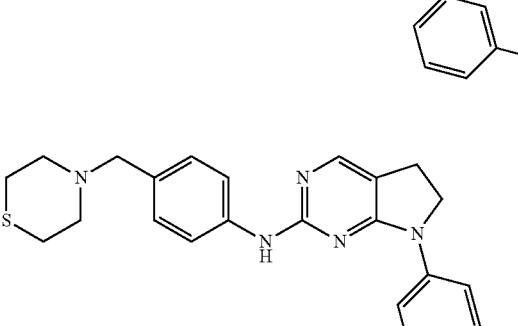 |
| I-13 | 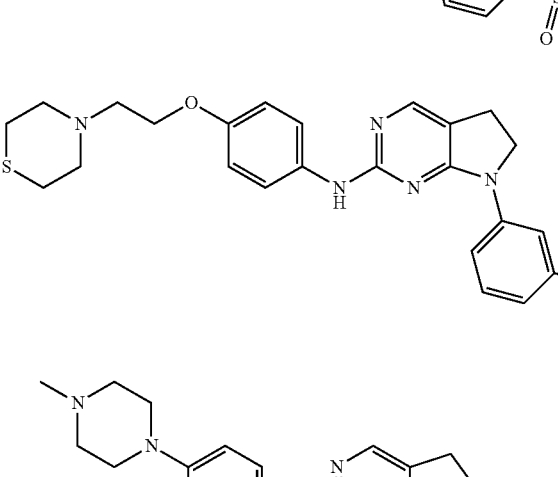 |
| I-14 | 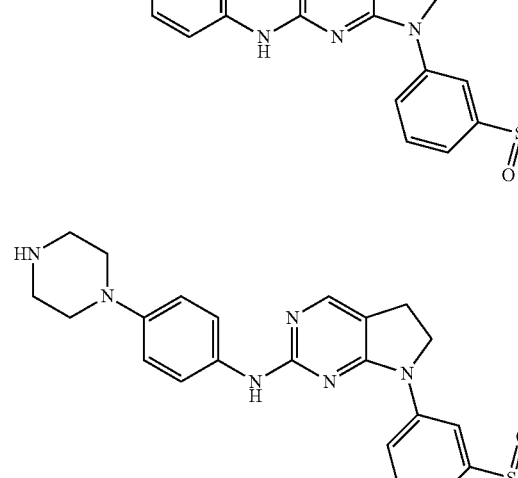 |
| I-15 |  |
| I-16 | |

Table 1-continued

| Compound | Structural formula |
|---|---|
| I-17 | |
| I-18 | |
| I-19 | |
| I-20 | |
| I-21 | |

Table 1-continued
| Compound | Structural formula |
|---|---|
| I-22 | 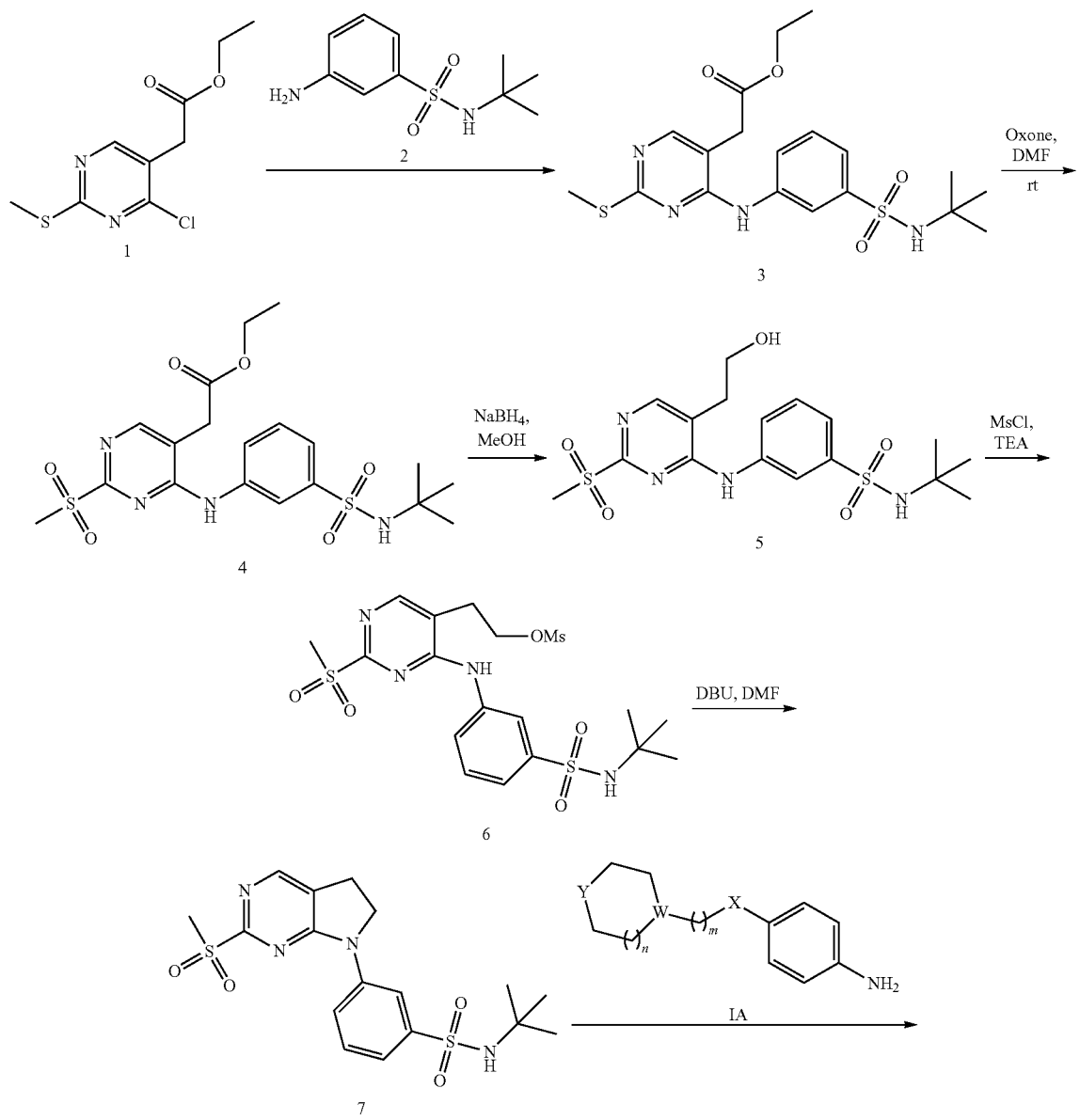 |
The second objective of the present invention is to provide a method for preparing the above compounds, which comprises the steps of:

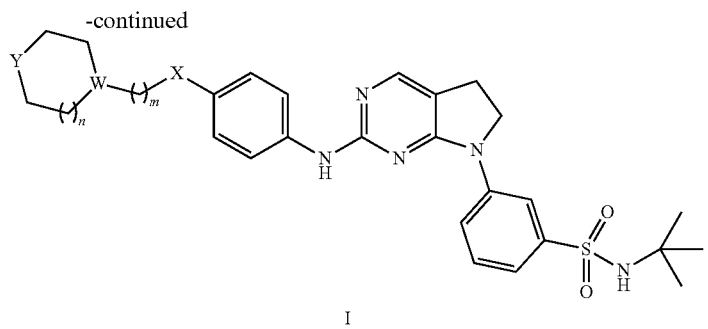

I (1) subjecting compounds 1 and 2 to a condensation reaction to give a compound 3;
(2) oxidizing the compound 3 with potassium hydrogen persulfate to give a compound 4;
(3) reducing the compound 4 with sodium borohydride to give a compound 5;
(4) activating the hydroxyl group of the compound 5 with methanesulfonyl chloride followed by a cyclization reaction to give a compound 7; and
(5) subjecting the compound 7 and a compound of formula IA to a condensation reaction to give the final product of formula I.

The definition of each group in step (5) is as described above.

The third objective of the present invention is to provide the use of the above compounds as novel JAK2 inhibitor in the preparation of medicaments for preventing or treating JAK-related diseases.

Preferably, the JAK-related diseases include: immune system diseases, including organ-graft rejection, such as allograft rejection and graft-versus-host disease; autoimmune diseases, including such as lupus, multiple sclerosis, rheumatoid arthritis, juvenile arthritis, psoriasis, ulcerative colitis, Crohn's disease, autoimmune thyroid disease, etc.; skin diseases, including such as psoriasis, itching, atopic dermatitis, etc.; allergic diseases, including such as asthma and rhinitis, etc.; viral diseases, including such as hepatitis B, hepatitis C and varicella-zoster virus; diabetes type I and diabetic complications; Alzheimer's disease, xerophthalmia, myelofibrosis, thrombocytosis, polycythemia, leukemia, multiple myeloma; cancers, including such as solid tumors (such as prostate cancer, kidney cancer, liver cancer, pancreatic cancer, gastric cancer, breast cancer, lung cancer, head and neck cancer, thyroid cancer, glioblastoma, melanoma, etc.), skin cancer (such as cutaneous T-cell lymphoma, cutaneous pericellular lymphoma, etc.); etc.

In the process of treating diseases, the compounds and derivatives thereof of the present invention can be used in the form of a composition for the treatment of related cancers and other diseases through oral administration, injection, etc. When used for oral administration, it can be prepared into conventional solid preparations such as tablets, powders, or capsules; and when used for injection, it can be prepared into parenteral solutions.

The fourth objective of the present invention is to provide a composition, comprising a therapeutically effective amount of the above pyrrolopyrimidine compound, stereoisomer thereof, or pharmaceutically acceptable salt thereof and a pharmaceutically acceptable carrier.

For example, the pharmaceutically acceptable salt may include metal salts, salts formed with organic bases, salts formed with inorganic acids, salts formed with organic acids, salts formed with basic or acidic amino acids, and the like. Non-limiting examples of the metal salts include, but are not limited to, alkali metal salts, such as sodium salts, potassium salts, etc.; alkaline earth metal salts, such as calcium salts, magnesium salts, barium salts, aluminum salts, etc. Non-limiting examples of the salts formed with inorganic acids include, but are not limited to, salts formed with hydrochloric acid, hydrobromic acid, nitric acid, sulfuric acid, phosphoric acid, and the like. Non-limiting examples of the salts formed with organic acids include, but are not limited to, salts formed with formic acid, acetic acid, trifluoroacetic acid, fumaric acid, oxalic acid, malic acid, maleic acid, tartaric acid, citric acid, succinic acid, methanesulfonic acid, benzenesulfonic acid, p-toluenesulfonic acid, and the like.

The carrier mentioned above refers to a conventional carrier in the pharmaceutical field, which includes: diluents, excipients such as water, etc.; binders such as cellulose derivatives, gelatin, polyvinylpyrrolidone, etc.; fillers such as starch, etc.; and disintegrating agents such as calcium carbonate and sodium bicarbonate. In addition, other auxiliary agents such as flavoring agents and sweetening agents may also be added to the composition.

Various dosage forms of the composition of the present invention can be prepared by conventional methods in the medical field, wherein the content of the active ingredient is 0.1% to 99.5% by weight.

The dosage of the composition of the present invention may vary depending on the route of administration, the age and weight of the patient, the type and severity of the disease to be treated, and the like. The daily dose is 0.001 to 30 mg/kg body weight for oral administration or 0.005 to 30 mg/kg body weight for injection.

Compared with the prior art, the pyrrolopyrimidine compounds, stereoisomers and pharmaceutically acceptable salts thereof provided by the present invention show better inhibitory activity for Janus Kinase and significantly better selectivity for JAK2 inhibitory targets. In addition, the preferred compounds of the present invention exhibit good pharmacokinetic properties and have the potential to be developed as selective JAK2 inhibitors.

DETAILED DESCRIPTION

The specific embodiments of the present invention will be described clearly and completely below. Obviously, the embodiments described below are only a part of, but not all, the embodiments of the present invention. Based on the embodiments of the present invention, all other embodiments obtained by those skilled in the art without creative work shall fall within the protection scope of the present invention.

Reference Example 1: Synthetic Route of General Intermediate 7

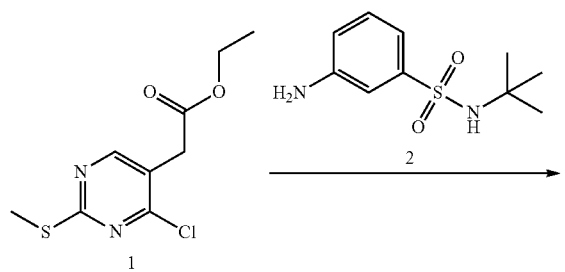

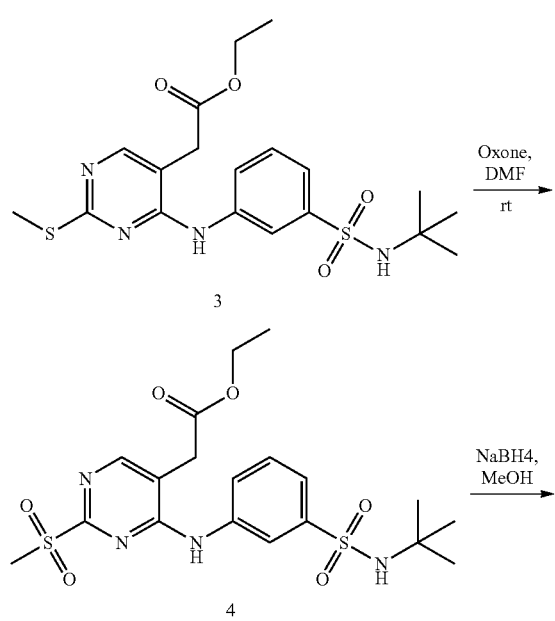

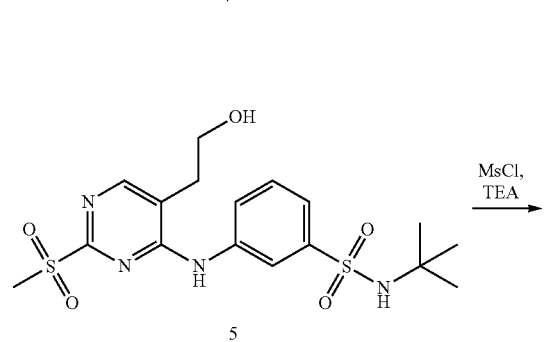

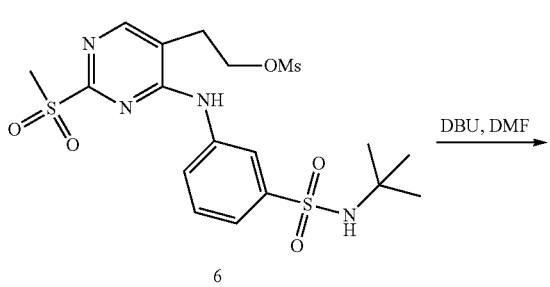

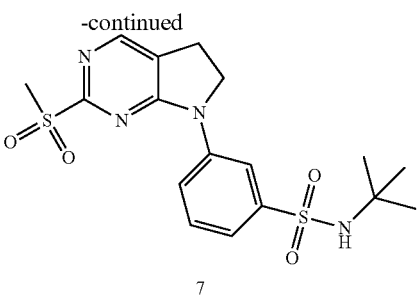

Procedures

Step 1: Synthesis of Intermediate 3

Compounds 1 (246 mg, 1.0 mmol) and 2 (228 mg, 1.0 mmol) were added to DMSO (8 mL) and subjected to microwave reaction at 150° C. for 2 h. The reaction mixture was concentrated to dryness under reduced pressure. The residue was purified by silica gel column chromatography (mobile phase: dichloromethane) to give yellow solid intermediate 3 (186 mg, yield 42%). $^1$HNMR (400 MHz, DMSO-d6): δ=8.97 (s, 1H), 8.17 (s, 1H), 8.08 (s, 1H), 7.87-7.81 (m, 1H), 7.54-7.46 (m, 3H), 4.10 (q, J=7.2 Hz, 2H), 3.79 (s, 2H), 2.44 (s, 3H), 1.21 (t, J=7.2 Hz, 3H), 1.12 (s, 9H). LCMS: MS Calcd.: 438.6, MS Found: 439.3.

Step 2: Synthesis of Intermediate 4

Potassium hydrogen persulfate (1.35 g, 2.2 mmol) was added to a solution of compound 3 (480 mg, 1.1 mmol) in DMF (20 mL). The reaction solution was stirred overnight at room temperature. The reaction was fully completed, monitored by LC-MS. The reaction mixture was concentrated to dryness under reduced pressure. The residue was purified by silica gel column chromatography (mobile phase: dichloromethane/methanol in 30/1) to give yellow solid intermediate 4 (220 mg, yield 43%). LCMS: MS Calcd.: 470.6, MS Found: 471.2.

Step 3: Synthesis of Intermediate 5

Sodium borohydride (184 mg, 4.84 mmol) was added to a solution of compound 4 (1.06 g, 2.42 mmol) in THF (60 mL). The reaction solution was stirred at room temperature overnight. The reaction was fully completed, monitored by LC-MS. The reaction mixture was concentrated to dryness under reduced pressure. The residue was purified by silica gel column chromatography (mobile phase: dichloromethane/methanol in 100/1 to 30/1) to give a white solid intermediate 5 (622 mg, yield 65%). LCMS: MS Calcd.: 428.5, MS Found: 429.2.

Step 4: Synthesis of Intermediate 6

Methanesulfonyl chloride (76 mg, 0.66 mmol) and triethylamine (100 mg, 0.99 mmol) were added to a solution of compound 4 (142 mg, 0.33 mmol) in dichloromethane (20 mL). The reaction solution was stirred at room temperature for 1 hour. The reaction was fully completed, monitored by LC-MS. The reaction mixture was concentrated to dryness under reduced pressure. The residue was purified by silica gel column chromatography (mobile phase: dichloromethane/methanol in 100/1 to 30/1) to give yellow solid intermediate 6 (122 mg, yield 72%). LCMS: MS Calcd.: 506.6, MS Found: 507.3.

Step 5: Synthesis of Intermediate 7

DBU (36 mg, 0.24 mmol) was added to a solution of compound 5 (122 mg, 0.24 mmol) in DMF (10 mL). The reaction solution was stirred at 80° C. for 1 hour. The reaction was fully completed, monitored by LC-MS. The reaction mixture was concentrated to dryness under reduced pressure. The residue was purified by prep-HPLC (NH4Ac as additive) to give a yellow solid intermediate 7 (36.4 mg, yield 39%). $^1$HNMR (400 MHz, CDCl$_3$): δ=8.50 (s, 1H), 8.24 (s, 1H), 7.92 (dd, J=1.6 Hz, 1H), 7.66 (d, J=8.0 Hz, 1H), 7.55 (t, J=8.0 Hz, 1H), 4.65 (m, 1H), 4.29 (s, 1H), 4.29 (t, J=8.8 Hz, 2H), 3.40-3.26 (m, 5H), 1.26 (s, 9H).

Example 1

Synthesis of Compound I-1

Synthetic Route

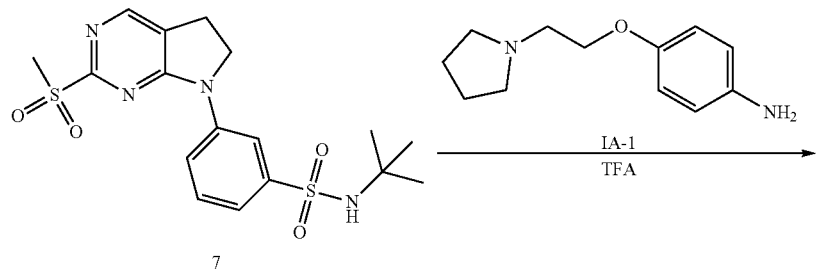

Procedures

Compounds 7 (20 mg, 0.05 mmol) and IA-1 (30 mg, 0.15 mmol) were added to trifluoroacetic acid (5 mL). The mixture was heated to 100° C. to react for 12 hours. The reaction was fully completed, monitored by LC-MS. The reaction mixture was concentrated to dryness under reduced pressure. The residue was purified by prep-HPLC (NH4Ac as additive) to give a gray solid I-1 (20.2 mg, yield 77%). $^1$HNMR (400 MHz, CD$_3$OD): δ=8.34 (s, 1H), 7.97 (d, J=8.4 Hz, 1H), 7.70 (s, 1H), 7.47-7.33 (m, 4H), 6.84 (d, J=8.8 Hz, 2H), 4.08-3.97 (m, 4H), 2.99 (t, J=8.4 Hz, 2H), 2.85 (t, J=5.2 Hz, 2H), 2.67-2.56 (m, 4H), 1.80-1.68 (m, 4H), 1.08 (s, 9H). LCMS: MS Calcd.: 536.7, MS Found: 537.0.

Example 2
Synthesis of Compound 1-2
Synthetic Route
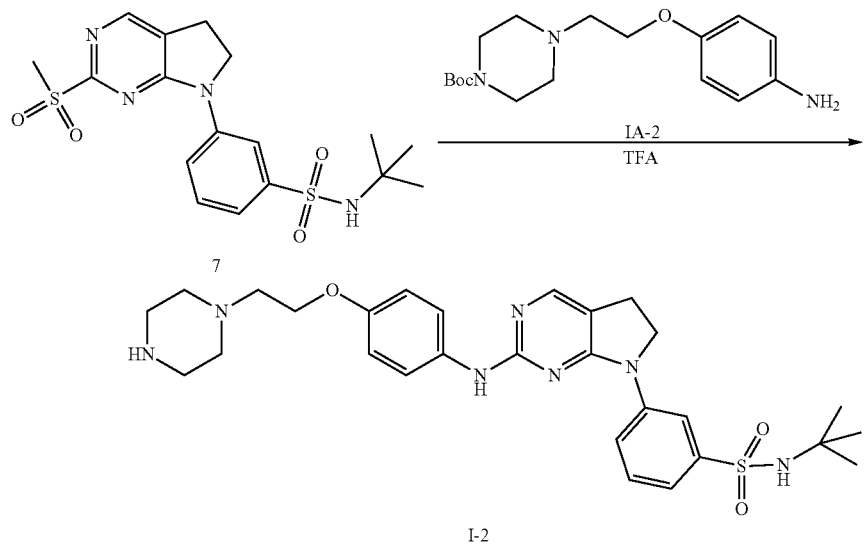
Procedures
See Example 1 for the procedures and purification methods, and the yield was 70%. $^1$HNMR (400 MHz, CD$_3$OD): δ=8.35 (s, 1H), 7.96 (d, J=8.0 Hz, 1H), 7.71 (s, 1H), 7.45-7.35 (m, 4H), 6.83 (d, J=8.8 Hz, 2H), 4.05-3.97 (m, 4H), 2.97 (t, J=8.4 Hz, 2H), 2.87 (t, J=5.6 Hz, 2H), 2.65-2.56 (m, 4H), 2.47-2.25 (m, 4H), 1.07 (s, 9H). LCMS: MS Calcd.: 551.7, MS Found: 552.3.
Example 3
Synthesis of Compound 1-3
Synthetic Route
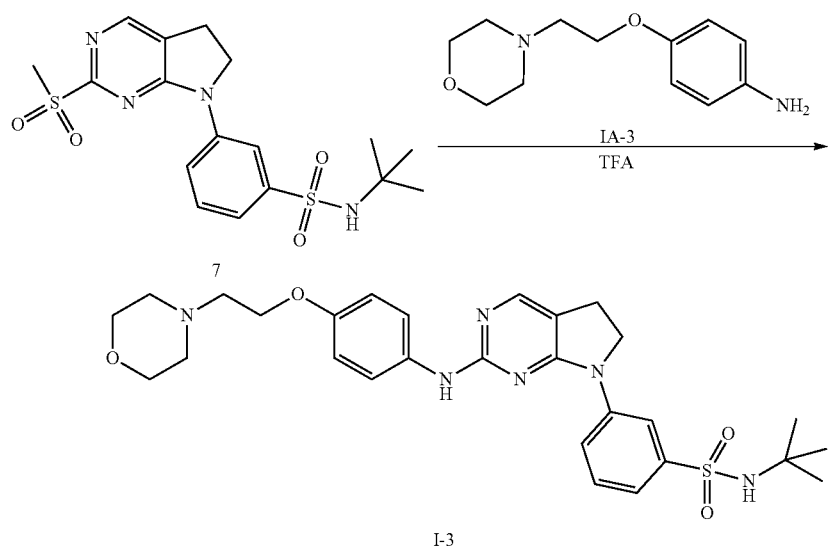

Procedures

See Example 1 for the procedures and purification methods, and the yield was 75%. ¹HNMR (400 MHz, CD$_3$OD): δ=8.33 (s, 1H), 7.95 (d, J=8.0 Hz, 1H), 7.73 (s, 1H), 7.44-7.35 (m, 4H), 6.82 (d, J=8.4 Hz, 2H), 4.06-3.97 (m, 4H), 3.87-3.59 (m, 4H), 2.98 (t, J=8.4 Hz, 2H), 2.87 (t, J=5.6 Hz, 2H), 2.45-2.28 (m, 4H), 1.09 (s, 9H). LCMS: MS Calcd.: 552.7, MS Found: 553.2.

Example 4

Synthesis of Compound 1-4

Synthetic Route

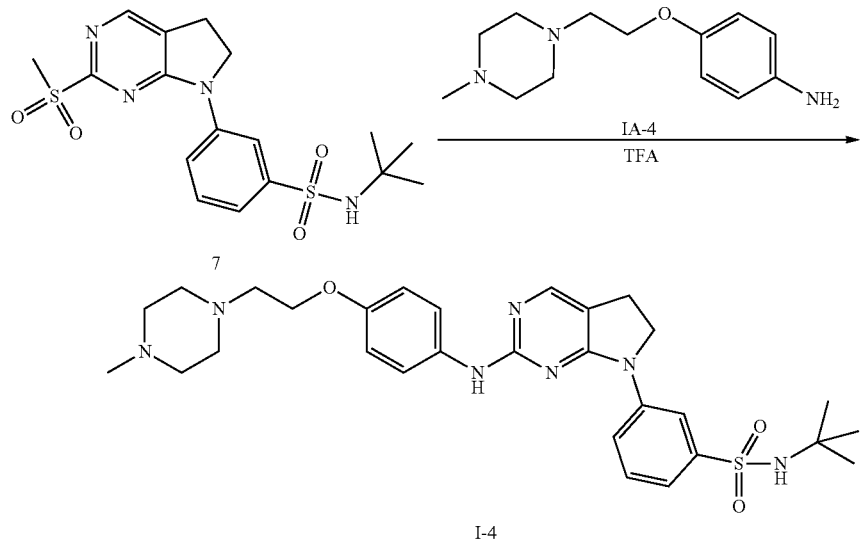

Procedures

See Example 1 for the procedures and purification methods, and the yield was 73%. ¹HNMR (400 MHz, CD$_3$OD): δ=8.37 (s, 1H), 7.97 (d, J=8.0 Hz, 1H), 7.72 (s, 1H), 7.46-7.37 (m, 4H), 6.82 (d, J=8.8 Hz, 2H), 4.06-3.97 (m, 4H), 2.96 (t, J=8.0 Hz, 2H), 2.88 (t, J=5.6 Hz, 2H), 2.67-2.56 (m, 4H), 2.48-2.27 (m, 4H), 2.25 (s, 3H), 1.05 (s, 9H). LCMS: MS Calcd.: 565.7, MS Found: 566.2.

Example 5

Synthesis of Compound 1-5

Synthetic Route

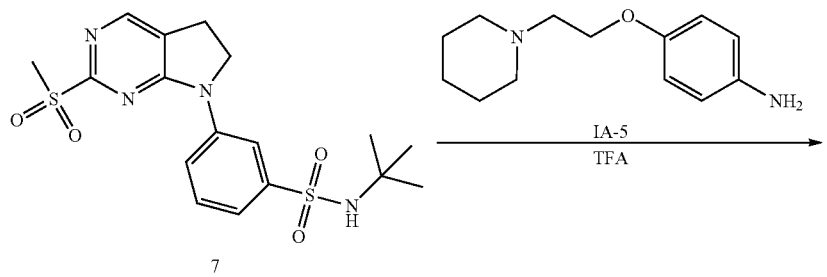

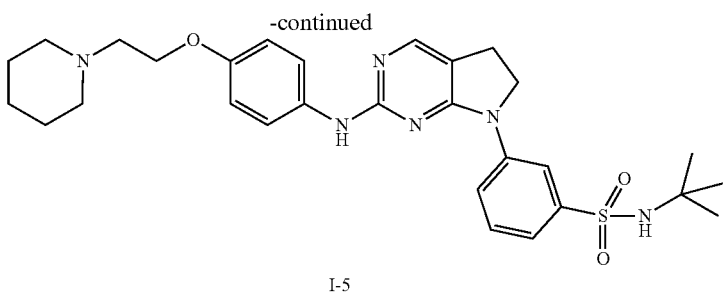

I-5

Procedures

See Example 1 for the procedures and purification methods, and the yield was 79%. ¹HNMR (400 MHz, CD₃OD): δ=8.33 (s, 1H), 7.93 (d, J=8.0 Hz, 1H), 7.70 (s, 1H), 7.43-7.31 (m, 4H), 6.80 (d, J=8.0 Hz, 2H), 4.07-3.98 (m, 4H), 2.97 (t, J=8.0 Hz, 2H), 2.88 (t, J=5.2 Hz, 2H), 2.49-2.31 (m, 4H), 1.67-1.52 (m, 6H), 1.07 (s, 9H). LCMS: MS Calcd.: 550.7, MS Found: 551.2.

Example 6

Synthesis of Compound 1-6

Synthetic Route

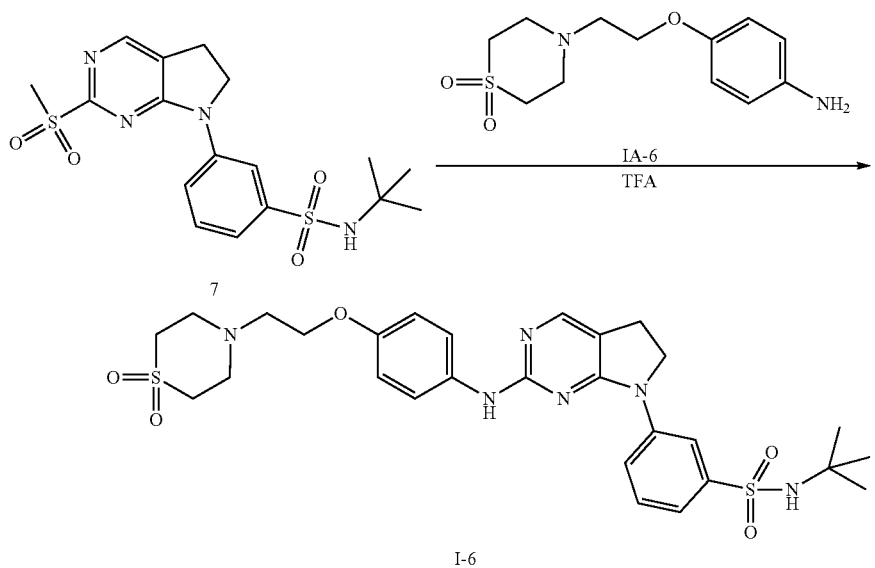

I-6

Procedures

See Example 1 for the procedures and purification methods, and the yield was 67%. ¹HNMR (400 MHz, CD₃OD): δ=8.34 (s, 1H), 7.95 (d, J=8.0 Hz, 1H), 7.72 (s, 1H), 7.43-7.32 (m, 4H), 6.83 (d, J=8.0 Hz, 2H), 4.09-3.98 (m, 4H), 3.69-3.57 (m, 4H), 2.98 (t, J=8.0 Hz, 2H), 2.93-2.89 (m, 4H), 2.85 (t, J=5.2 Hz, 2H), 1.07 (s, 9H). LCMS: MS Calcd.: 600.7, MS Found: 601.2.

Example 7
Synthesis of Compound I-7
Synthetic Route
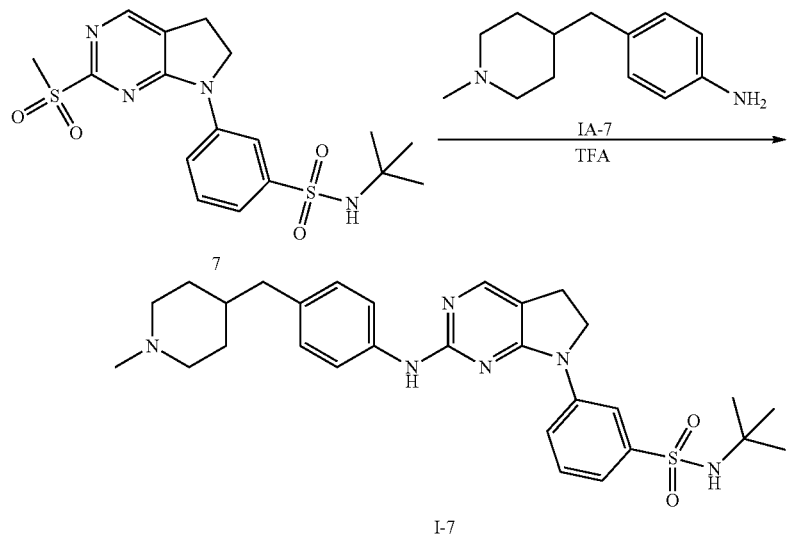
Procedures
See Example 1 for the procedures and purification methods, and the yield was 75%. $^1$HNMR (400 MHz, CD$_3$OD): δ=8.33 (s, 1H), 7.93 (m, 1H), 7.71 (s, 1H), 7.43-7.31 (m, 4H), 6.82 (d, J=8.0 Hz, 2H), 4.10 (t, J=8.0 Hz, 2H), 2.97 (t, J=8.0 Hz, 2H), 2.57-2.43 (m, 6H), 2.29 (s, 3H), 1.81-1.63 (m, 5H), 1.08 (s, 9H). LCMS: MS Calcd.: 534.7, MS Found: 535.3.
Example 8
Synthesis of Compound I-8
Synthetic Route
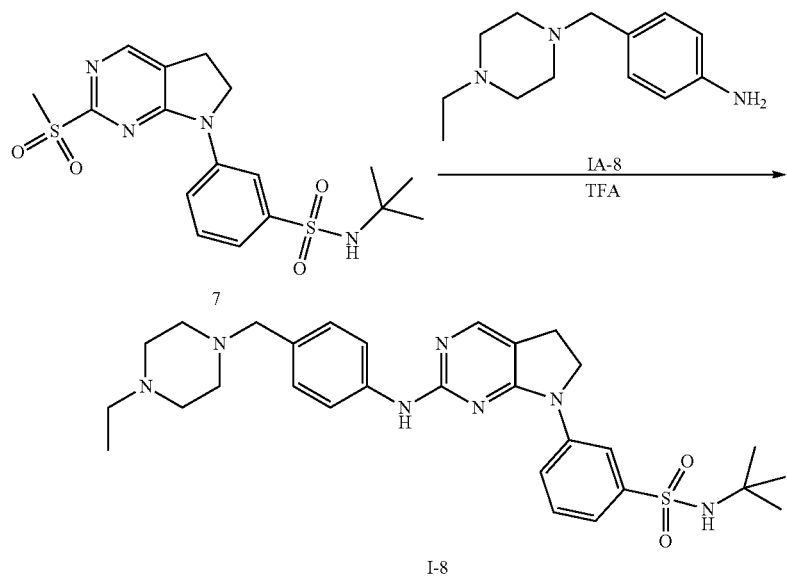

Procedures

See Example 1 for the procedures and purification methods, and the yield was 78%. ¹HNMR (400 MHz, CD$_3$OD): δ=8.35 (s, 1H), 7.94 (d, J=8.0 Hz, 1H), 7.72 (s, 1H), 7.45-7.31 (m, 4H), 6.86 (d, J=8.0 Hz, 2H), 4.13 (t, J=8.0 Hz, 2H), 3.69 (s, 2H), 2.99 (t, J=8.0 Hz, 2H), 2.56-2.38 (m, 10H), 1.09 (s, 9H), 1.03 (m, 3H). LCMS: MS Calcd.: 549.7, MS Found: 550.3.

Example 9

Synthesis of Compound I-9

Synthetic Route

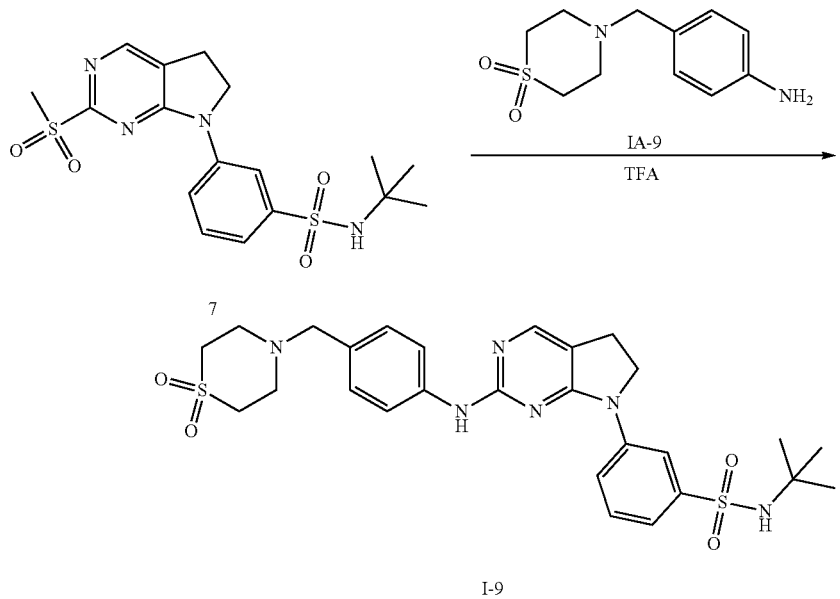

Procedures

See Example 1 for the procedures and purification methods, and the yield was 71%. ¹HNMR (400 MHz, CD$_3$OD): δ=8.31 (s, 1H), 7.92 (d, J=8.0 Hz, 1H), 7.70 (s, 1H), 7.44-7.29 (m, 4H), 6.85 (d, J=8.0 Hz, 2H), 4.12 (t, J=8.0 Hz, 2H), 3.69 (s, 2H), 3.51-3.37 (m, 4H), 2.97 (t, J=8.0 Hz, 2H), 2.87-2.78 (m, 4H), 1.09 (s, 9H). LCMS: MS Calcd.: 570.7, MS Found: 571.3.

Example 10

Synthesis of Compound I-10

Synthetic Route

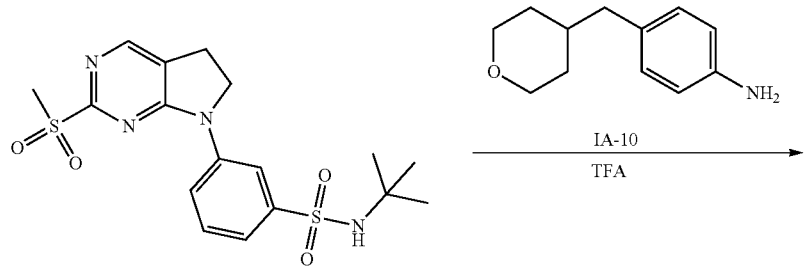

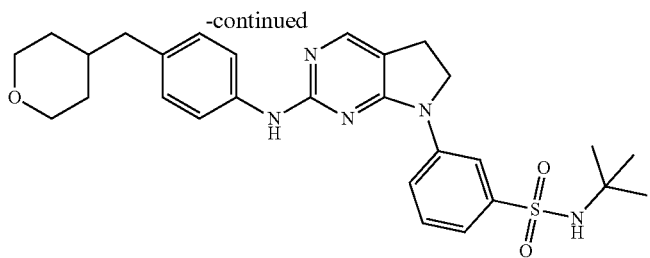

I-10

Procedures

See Example 1 for the procedures and purification methods, and the yield was 75%. ¹HNMR (400 MHz, CD$_3$OD): δ=8.34 (s, 1H), 7.91 (m, 1H), 7.70 (s, 1H), 7.42-7.31 (m, 4H), 6.84 (d, J=8.0 Hz, 2H), 4.12 (t, J=8.0 Hz, 2H), 3.72-3.55 (m, 4H), 2.97 (t, J=8.0 Hz, 2H), 2.45 (s, 2H), 1.81-1.62 (m, 5H), 1.06 (s, 9H). LCMS: MS Calcd.: 521.7, MS Found: 522.3.

Example 11

Synthesis of Compound I-11

Synthetic Route

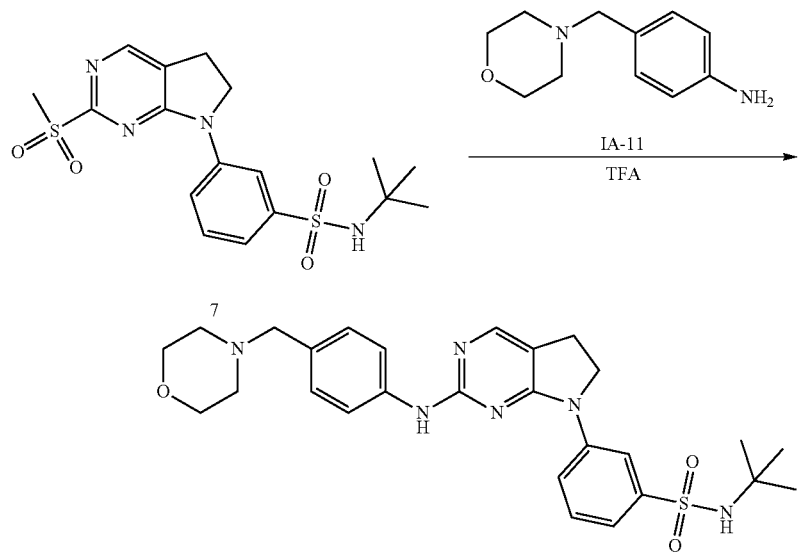

I-11

Procedures

See Example 1 for the procedures and purification methods, and the yield was 71%. ¹HNMR (400 MHz, CD$_3$OD): δ=8.33 (s, 1H), 7.92 (d, J=8.0 Hz, 1H), 7.73 (s, 1H), 7.41-7.29 (m, 4H), 6.84 (d, J=8.0 Hz, 2H), 4.13 (t, J=8.0 Hz, 2H), 3.69-3.65 (m, 6H), 2.97 (t, J=8.0 Hz, 2H), 2.55-2.48 (m, 4H), 1.05 (s, 9H). LCMS: MS Calcd.: 522.7, MS Found: 523.1.

Example 12
Synthesis of Compound 1-12
Synthetic Route
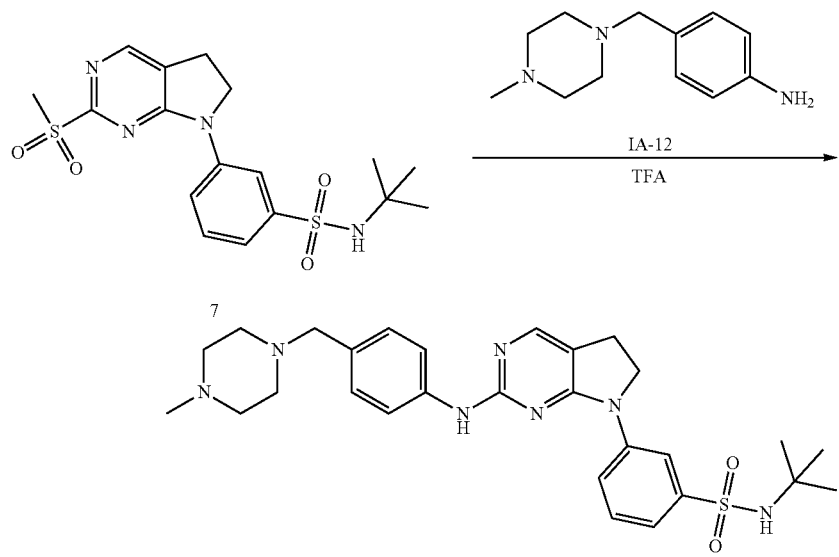
Procedures
See Example 1 for the procedures and purification methods, and the yield was 68%. ¹HNMR (400 MHz, CD$_3$OD): δ=8.31 (s, 1H), 7.92 (d, J=8.0 Hz, 1H), 7.69 (s, 1H), 7.42-7.31 (m, 4H), 6.83 (d, J=8.0 Hz, 2H), 4.14 (t, J=8.0 Hz, 2H), 3.67 (s, 2H), 3.03 (t, J=8.0 Hz, 2H), 2.49-2.38 (m, 8H), 2.30 (s, 3H), 1.06 (s, 9H). LCMS: MS Calcd.: 535.7, MS Found: 536.3.
Example 13
Synthesis of Compound 1-13
Synthetic Route

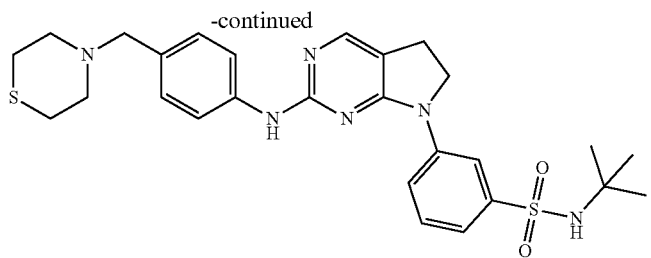

I-13

Procedures

See Example 1 for the procedures and purification methods, and the yield was 65%. ¹HNMR (400 MHz, CD₃OD): δ=8.32 (s, 1H), 7.92 (d, J=8.0 Hz, 1H), 7.70 (s, 1H), 7.40-7.29 (m, 4H), 6.83 (d, J=8.0 Hz, 2H), 4.12 (t, J=8.0 Hz, 2H), 3.67 (s, 2H), 2.95 (t, J=8.0 Hz, 2H), 2.53-2.43 (m, 8H), 1.07 (s, 9H). LCMS: MS Calcd.: 538.7, MS Found: 539.1.

Example 14

Synthesis of Compound 1-14

Synthetic Route

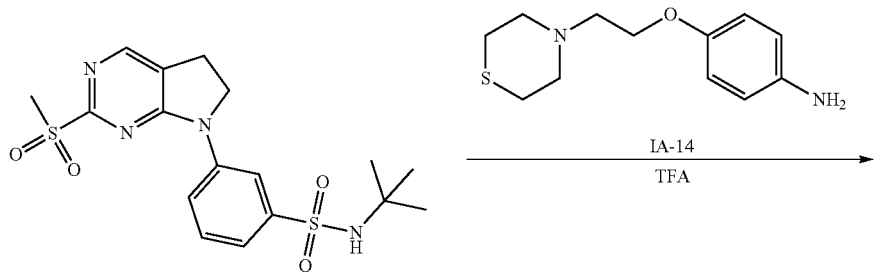

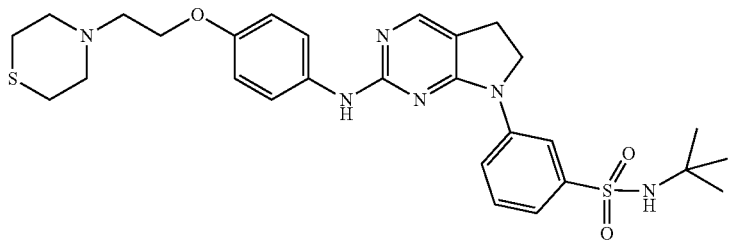 [SMILES: CC(C)(C)NS(=O)(=O)c1cccc(N2CCc3cnc(Nc4ccc(OCCN5CCCCC5)cc4)nc32)c1]

I-14

Procedures

See Example 1 for the procedures and purification methods, and the yield was 75%. ¹HNMR (400 MHz, CD₃OD): δ=8.32 (s, 1H), 7.90 (d, J=8.0 Hz, 1H), 7.75 (s, 1H), 7.42-7.35 (m, 4H), 6.83 (d, J=8.4 Hz, 2H), 4.07-3.97 (m, 4H), 3.89-3.67 (m, 4H), 2.97 (t, J=8.4 Hz, 2H), 2.82 (t, J=5.6 Hz, 2H), 2.46-2.28 (m, 4H), 1.08 (s, 9H). LCMS: MS Calcd.: 568.7, MS Found: 569.2.

Example 15
Synthesis of Compound 1-15
Synthetic Route
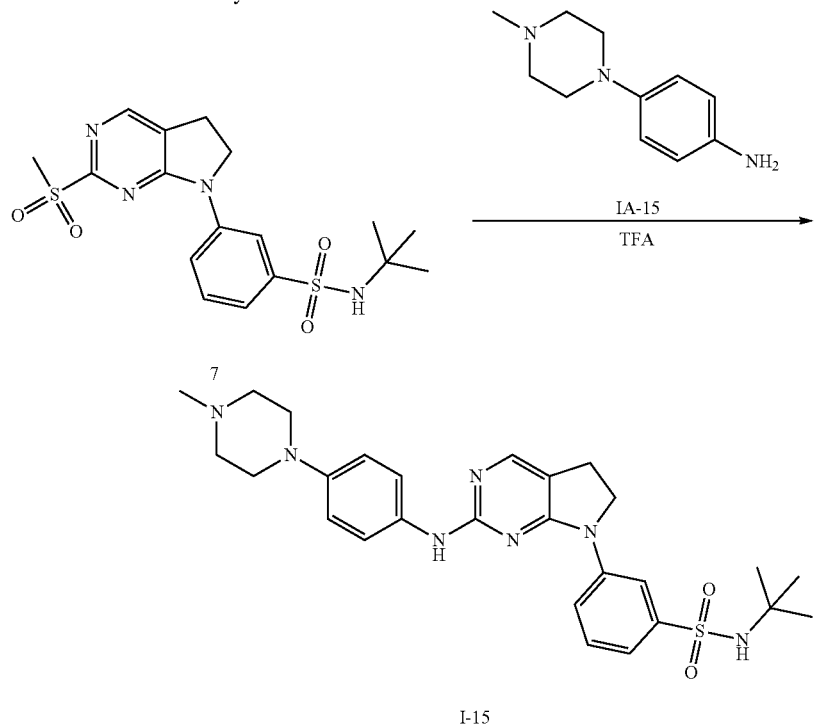
Procedures
See Example 1 for the procedures and purification methods, and the yield was 73%. ¹HNMR (400 MHz, CD₃OD): δ=8.38 (s, 1H), 7.96 (d, J=8.0 Hz, 1H), 7.71 (s, 1H), 7.48-7.33 (m, 4H), 6.91 (d, J=9.2 Hz, 2H), 4.05 (t, J=8.4 Hz, 2H), 3.12-3.15 (m, 4H), 3.01 (t, J=8.0 Hz, 2H), 2.58-2.48 (m, 4H), 2.26 (s, 3H), 1.07 (s, 9H). LCMS: MS Calcd.: 521.7, MS Found: 522.0.
Example 16
Synthesis of Compound 1-16
Synthetic Route
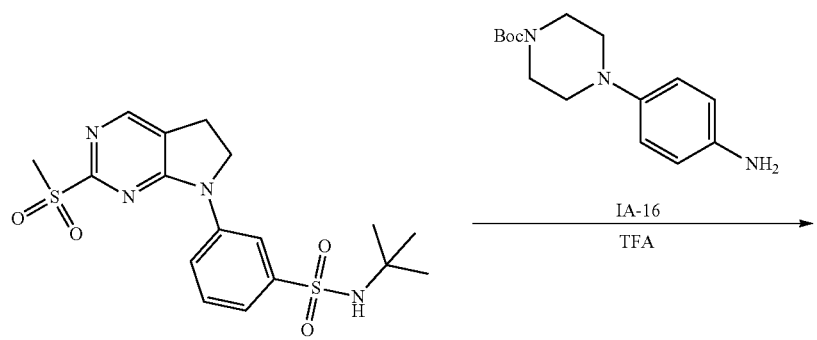

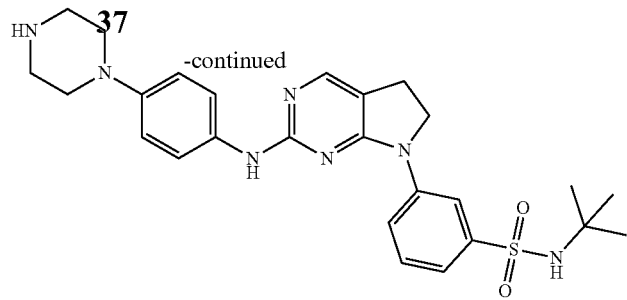

I-16

Procedures

See Example 1 for the procedures and purification methods, and the yield was 70%. $^1$HNMR (400 MHz, CD$_3$OD): δ=8.35 (s, 1H), 7.95 (d, J=8.0 Hz, 1H), 7.70 (s, 1H), 7.49-7.33 (m, 4H), 6.90 (d, J=9.2 Hz, 2H), 4.09 (t, J=8.4 Hz, 2H), 3.52-3.45 (m, 4H), 2.98 (t, J=8.0 Hz, 2H), 2.68-2.57 (m, 4H), 1.07 (s, 9H). LCMS: MS Calcd.: 507.7, MS Found: 508.2.

Example 17

Synthesis of Compound I-17

Synthetic Route

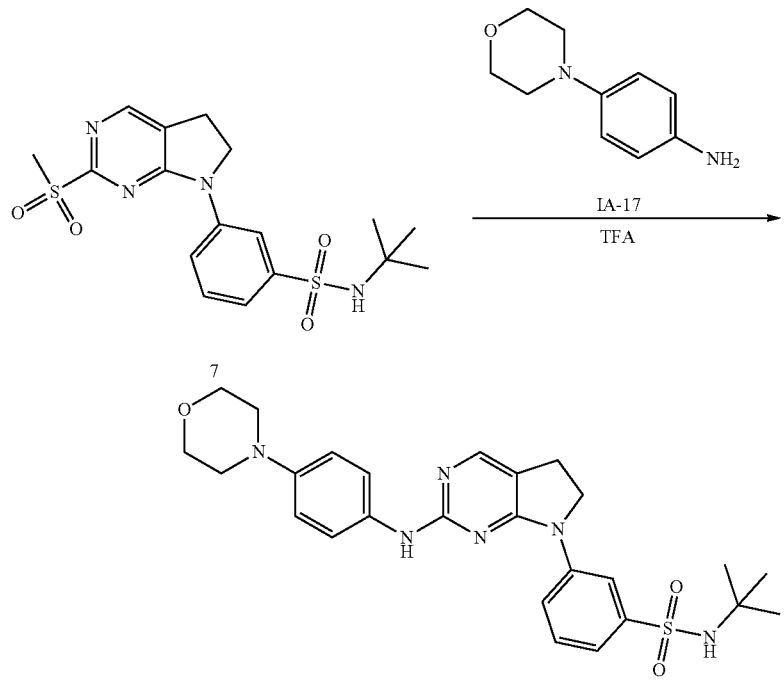

I-17

Procedures

See Example 1 for the procedures and purification methods, and the yield was 63%. $^1$HNMR (400 MHz, CD$_3$OD): δ=8.34 (s, 1H), 7.93 (d, J=8.0 Hz, 1H), 7.71 (s, 1H), 7.48-7.33 (m, 4H), 6.90 (d, J=9.2 Hz, 2H), 4.13 (t, J=8.4 Hz, 2H), 3.79-3.60 (m, 4H), 3.25-3.12 (m, 4H), 2.99 (t, J=8.0 Hz, 2H), 1.09 (s, 9H). LCMS: MS Calcd.: 508.6, MS Found: 509.2.

Example 18
Synthesis of Compound 1-18
Synthetic Route
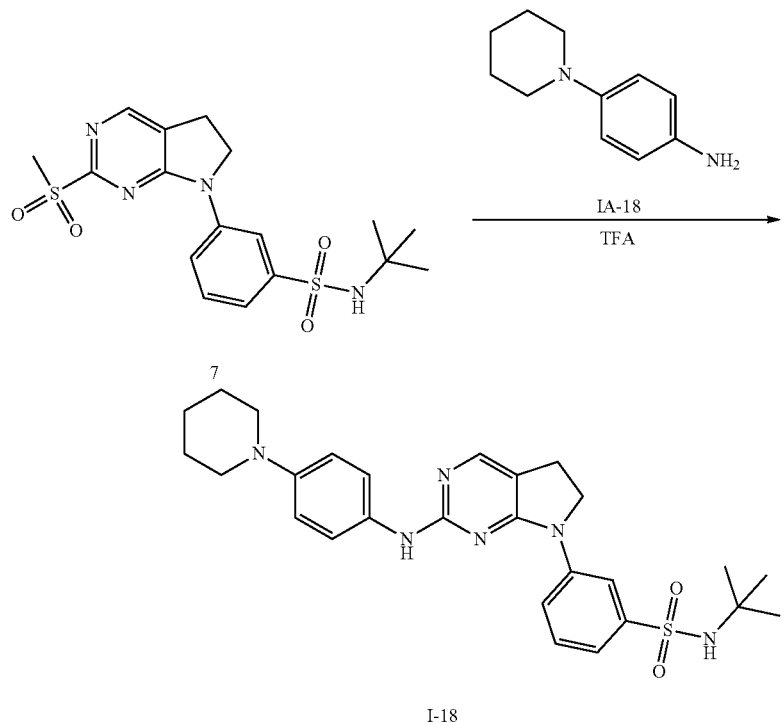
Procedures
See Example 1 for the procedures and purification methods, and the yield was 73%. $^1$HNMR (400 MHz, CD$_3$OD): δ=8.35 (s, 1H), 7.92 (d, J=8.0 Hz, 1H), 7.70 (s, 1H), 7.47-7.31 (m, 4H), 6.93 (d, J=9.2 Hz, 2H), 4.12 (t, J=8.0 Hz, 2H), 3.59-3.40 (m, 4H), 2.97 (t, J=8.0 Hz, 2H), 1.59-1.43 (m, 5H), 1.07 (s, 9H). LCMS: MS Calcd.: 506.7, MS Found: 507.2.
Example 19
Synthesis of Compound 1-19
Synthetic Route
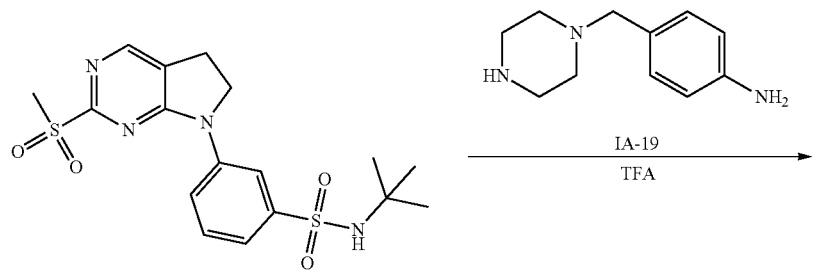

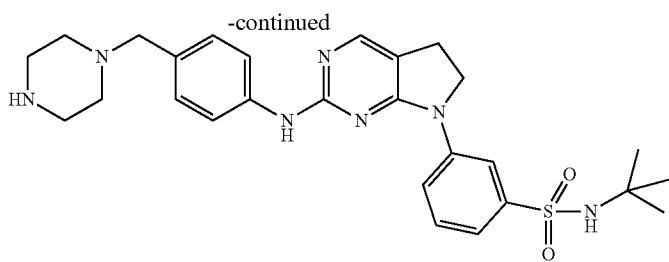

I-19

Procedures

See Example 1 for the procedures and purification methods, and the yield was 76%. ¹HNMR (400 MHz, CD₃OD): δ=8.34 (s, 1H), 7.91 (d, J=8.0 Hz, 1H), 7.75 (s, 1H), 7.45-7.31 (m, 4H), 6.91 (d, J=9.2 Hz, 2H), 4.13 (t, J=8.0 Hz, 2H), 3.75 (m, 1H), 2.98 (t, J=8.0 Hz, 2H), 2.68-2.50 (m, 4H), 2.20-2.13 (m, 4H), 1.08 (s, 9H). LCMS: MS Calcd.: 522.7, MS Found: 523.2.

Example 20

Synthesis of Compound 1-20

Synthetic Route

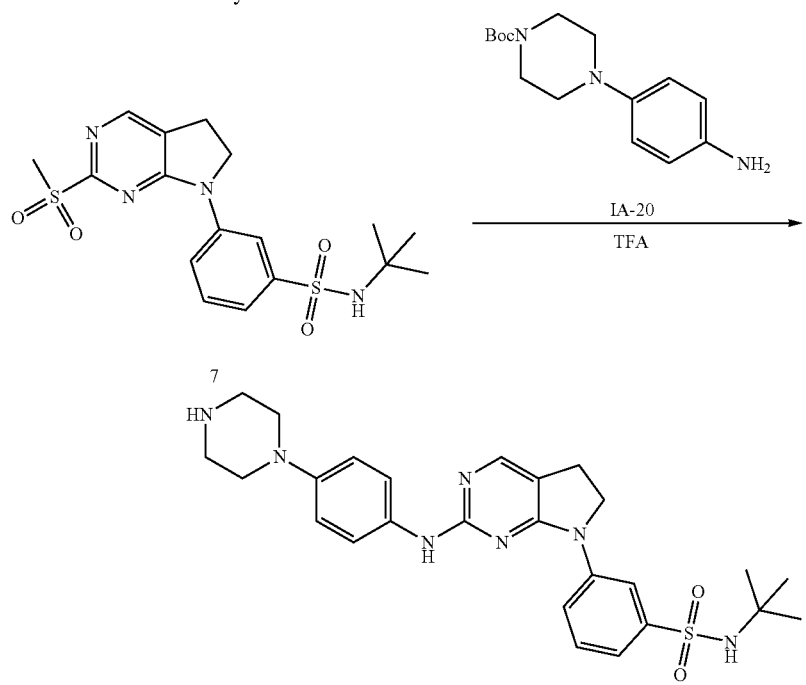

I-20

Procedures

See Example 1 for the procedures and purification methods, and the yield was 79%. ¹HNMR (400 MHz, CD₃OD): δ=8.33 (s, 1H), 7.91 (d, J=8.0 Hz, 1H), 7.70 (s, 1H), 7.49-7.33 (m, 4H), 6.93 (d, J=9.2 Hz, 2H), 4.10 (t, J=8.0 Hz, 2H), 2.97 (t, J=8.0 Hz, 2H), 2.79-2.60 (m, 5H), 2.10-1.98 (m, 4H), 1.07 (s, 9H). LCMS: MS Calcd.: 506.7, MS Found: 507.2.

Example 21
Synthesis of Compound 1-21
Synthetic Route
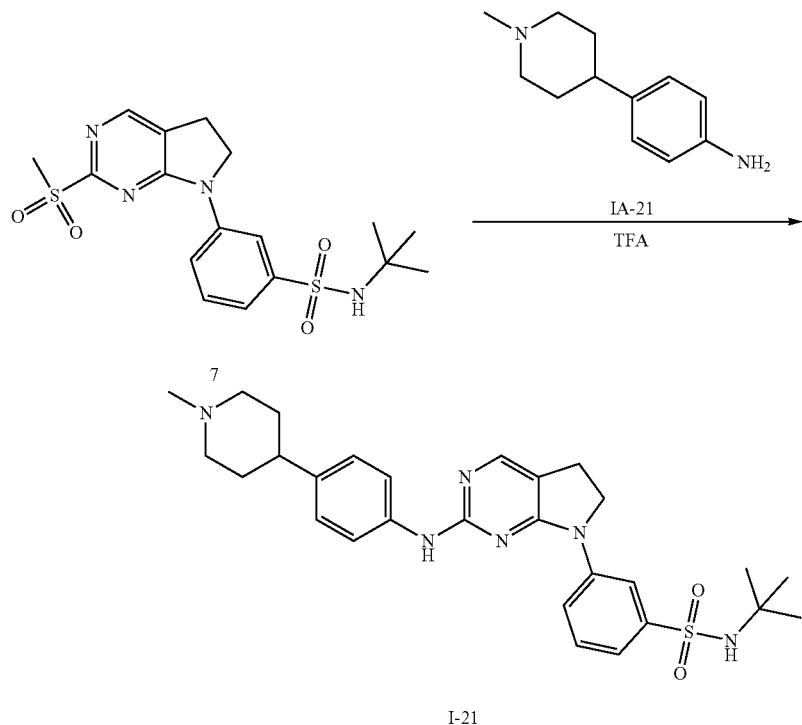
I-21
Procedures
See Example 1 for the procedures and purification methods, and the yield was 77%. $^1$HNMR (400 MHz, CD$_3$OD): δ=8.32 (s, 1H), 7.93 (d, J=8.0 Hz, 1H), 7.71 (s, 1H), 7.47-7.32 (m, 4H), 6.91 (d, J=8.8 Hz, 2H), 4.13 (t, J=8.0 Hz, 2H), 3.03 (t, J=8.0 Hz, 2H), 2.79 (m, 1H), 2.49-2.35 (m, 4H), 2.27 (s, 3H), 1.89-1.75 (m, 4H), 1.05 (s, 9H). LCMS: MS Calcd.: 520.7, MS Found: 521.2.
Example 22
Synthesis of Compound 1-22
Synthetic Route
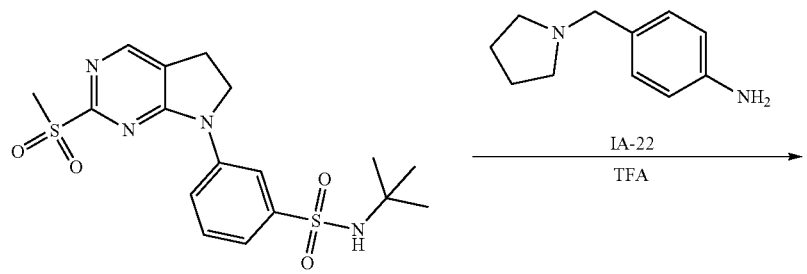

-continued

I-22

Procedures

See Example 1 for the procedures and purification methods, and the yield was 76%. $^1$HNMR (400 MHz, CD$_3$OD): δ=8.33 (s, 1H), 7.91 (d, J=8.0 Hz, 1H), 7.72 (s, 1H), 7.43-7.29 (m, 4H), 6.85 (d, J=8.0 Hz, 2H), 4.14 (t, J=8.0 Hz, 2H), 3.69 (s, 2H), 2.97 (t, J=8.0 Hz, 2H), 2.51-2.43 (m, 4H), 1.67-1.52 (m, 4H), 1.08 (s, 9H). LCMS: MS Calcd.: 506.7, MS Found: 507.2.

Biological Tests

Test Example 1: Activity Tests on JAK1, JAK2 and JAK3

Compound Preparation

The compound was dissolved in 100% DMSO, prepared as a 10 mM stock solution, and frozen at −20° C.

Kinase Reaction Process:

(1) 1×Kinase buffer was prepared.

(2) Preparation of compound concentration gradients: the starting concentration of the test compound was 500 nM, and was diluted with 100% DMSO in a 384-well Source plate to give a solution having a concentration of 100 folds of the final concentration. The compound was diluted 3 times, 9 times, 27 times . . . with Precision to obtain 12 concentration gradients. A pipette Echo 550 was used to transfer 250 nL of the compound solution having a concentration of 100 folds of the final concentration to the target plate OptiPlate-384F.

(3) A kinase solution having a concentration of 2.5 folds of the final concentration was prepared with 1×Kinase buffer.

(4) 10 μL of kinase solution having a concentration of 2.5 folds of the final concentration was added to the compound well and the positive control well. 10 μL of 1×Kinase buffer was added to the negative control well.

(5) Centrifugation was performed at 1000 rpm for 30 seconds. The reaction plate was shaken well, and incubated at room temperature for 10 minutes.

(6) A mixed solution of ATP and kinase substrate (having a concentration of 5 and 3 folds of the final concentration, respectively) was prepared with 1×Kinase buffer.

(7) 15 μL of the mixed solution as prepared in (6) was added to initiate the reaction.

(8) The 384-well plate was centrifuged at 1000 rpm for 30 seconds, shaken well, and incubated at room temperature for the corresponding time.

(9) 30 μL of stop buffer was added to terminate the kinase reaction. The mixture was then centrifuged at 1000 rpm for 30 seconds, and shaken well.

(10) Caliper EZ Reader was used to read the conversion rate.

Data Analysis

Calculation Equation:

$$\% \text{ Inhibition} = \frac{\text{Conversion \%\_max} - \text{Conversion \%\_sample}}{\text{Conversion \%\_max} - \text{Conversion \%\_min}} \times 100$$

Wherein:

Conversion %_sample represents the conversion rate of the sample;

Conversion %_min represents the conversion rate of the well without enzyme activity, which is a mean value of the negative control wells; and Conversion %_max represents the conversion rate of the well without compound inhibition, which is a mean value of the positive control wells.

Fitted Dose-Response Curve:

The log value of the concentration is taken as the X axis, the % inhibition rate is taken as the Y axis, and the log(inhibitor) vs. response—Variable slope of the analysis software GraphPad Prism 5 was used to fit the dose-response curve to obtain the IC$_{50}$ value of each compound on the enzyme activity. The calculation equation is:

$$Y = \text{Bottom} + (\text{Top} - \text{Bottom})/(1 + 10^{((\text{Log IC}_{50} - X)*\text{Hill Slope})})$$

The above experimental results are shown in Table 2.

TABLE 2

Enzyme test results of the compounds

| Compound | JAK1 (nM) | JAK2 (nM) | JAK3 (nM) | JAK1/ JAK2 | JAK3/ JAK2 |
|---|---|---|---|---|---|
| Baricitinib | 6.2 | 5.9 | 10 | 1.1 | 1.7 |
| Ruxolitinib | 2.8 | 2.5 | 7 | 1.1 | 2.8 |
| Fedratinib | 70 | 4 | 330 | 17.5 | 82.5 |
| I-1 | 210 | 2.5 | 1260 | 84 | 504 |
| I-2 | 189 | 1.1 | 980 | 172 | 891 |
| I-3 | 100 | 1.0 | 877 | 100 | 877 |
| I-4 | 105 | 1.2 | 1020 | 87 | 850 |
| I-5 | 99 | 1.1 | 1230 | 90 | 1118 |
| I-6 | 97 | 0.75 | 890 | 129 | 1187 |
| I-7 | 103 | 0.9 | 900 | 114 | 1000 |
| I-8 | 151 | 1.2 | 1000 | 126 | 833 |
| I-9 | 191 | 1.7 | 1330 | 112 | 782 |
| I-10 | 100 | 0.5 | 987 | 200 | 1974 |
| I-11 | 105 | 0.8 | 980 | 131 | 1225 |
| I-12 | 98 | 0.7 | 879 | 140 | 1256 |
| I-13 | 89 | 1.0 | 865 | 89 | 865 |
| I-14 | 102 | 1.1 | 998 | 93 | 907 |
| I-15 | 72 | 0.73 | 598 | 99 | 819 |

TABLE 2-continued

Enzyme test results of the compounds

| Compound | JAK1 (nM) | JAK2 (nM) | JAK3 (nM) | JAK1/ JAK2 | JAK3/ JAK2 |
|---|---|---|---|---|---|
| I-16 | 203 | 2.0 | 1390 | 101 | 695 |
| I-17 | 221 | 2.2 | 1560 | 100 | 709 |
| I-18 | 109 | 0.7 | 1112 | 156 | 1588 |
| I-19 | 121 | 0.9 | 1520 | 134 | 1689 |
| I-20 | 130 | 1.0 | 1433 | 130 | 1433 |
| I-21 | 101 | 0.8 | 988 | 126 | 1235 |
| I-22 | 105 | 0.6 | 873 | 175 | 1455 |

Note:
The results of the controls and the compounds of the present invention were measured under the same experimental conditions.

Conclusion: The compounds of the present invention exhibited better selectivity for JAK2 targets when compared to the positive controls Baricitinib, Ruxolitinib and Fedratinib.

Test Example 2: Cell Proliferation Experiment

HEL92.1.7 Cell Proliferation Experiment

Procedures (1) Seeding
  a. cells were digested, resuspended, and counted with an automatic cell counter;
  b. the cell suspension was diluted to the required density; and
  c. 100 μL cells was seeded in each well and incubated overnight at 37° C.
(2) Compounds Preparation
  a. the compound was formulated into a diluted solution having a concentration of 200 folds of the final concentration; and
  b. the diluted solution was diluted with culture media to prepare a compound solution having a concentration of 3 folds of the final concentration. 50 μL of compound solution was added to each well. DMSO of the same volume was added to the control well. These wells were incubated at 37° C., 5% $CO_2$ for 72 hours.
(3) Detection
  a. the cell plate was equilibrated to room temperature;
  b. 40 μL of Cell Titer-Glo® reagent was added to each well, shaked for 2 minutes, and placed for 10 minutes; and
  c. EnVision was used for detection.
Data Analysis:
  (1) GraphPad Prism 5 was used to calculate $IC_{50}$
  (2) % Inh=(Max signal−Compound signal)/(Max signal−Min signal)×100.
  (3) Max signal represents the positive control well, which only contains DMSO. The volume of DMSO is equal to that of the compound solution.
  (4) Min signal represents the negative control well, which only contains culture media.

TF-1 Cell Proliferation Experiment (1) Seeding
  a. Complete medium was prepared.
  b. Cells were thawed and cultured.
  c. Cells were centrifuged, resuspended, counted and seeded. The culture plate was placed in a $CO_2$ incubator overnight.

(2) Preparation and Addition of Compounds
  a. The compound was prepared with DMSO as a 10 mM stock solution. It was diluted to a working concentration, and then gradually diluted to obtain compound solutions with multiple concentration gradients.
  b. 0.5 μL was pipetted from the corresponding compound plate and added to the cell culture plate for overnight culture.
  c. The plate was incubated in a 37° C. incubator for 72 hours.
(3) Detection and Analysis
  a. CellTiter Glo assay reagent was prepared.
  b. The assay reagent was added to the culture plate, mixed well, and placed. Then, the plate was read.

% Inhibition=(1−(corresponding well value−average value of BLANK)/(average value of DMSO control−average value of BLANK))*100%

The curve fitting tool (XL fit) was used for data analysis (XL fit software: Fit model: Dose response one site/F(x) 205 [fit=(A+4B−A)/(1+((C/x)^D)))]).

The above experimental results are shown in Table 3.

TABLE 3

Test results of cell proliferation experiments

| Compound | HEL92.1.7 (μM) | TF-1 (μM) |
|---|---|---|
| Fedratinib | 0.58 | 1.57 |
| Ruxolitinib | 1.12 | 0.32 |
| I-1 | 0.23 | 0.15 |
| I-2 | 0.30 | 0.21 |
| I-3 | 0.19 | 0.18 |
| I-4 | 0.34 | 0.18 |
| I-5 | 0.18 | 0.22 |
| I-6 | 0.35 | 0.15 |
| I-7 | 0.25 | 0.19 |
| I-8 | 0.33 | 0.23 |
| I-9 | 0.17 | 0.21 |
| I-10 | 0.20 | 0.19 |
| I-11 | 0.24 | 0.17 |
| I-12 | 0.22 | 0.20 |
| I-13 | 0.31 | 0.27 |
| I-14 | 0.43 | 0.28 |
| I-15 | 0.17 | 0.12 |
| I-16 | 0.21 | 0.15 |
| I-17 | 0.25 | 0.14 |
| I-18 | 0.20 | 0.15 |
| I-19 | 0.21 | 0.17 |
| I-20 | 0.25 | 0.19 |
| I-21 | 0.22 | 0.15 |
| I-22 | 0.24 | 0.22 |

Note:
The results of the controls and the compounds of the present invention were measured under the same experimental conditions.

Conclusion: The compounds of the present invention exhibited better proliferation inhibitory activity on HEL92.1.7 and TF-1 when compared to the controls Fedratinib and Ruxolitinib.

Test Example 3: Pharmacokinetic Test of the Compounds of the Present Invention

SD rats were used as the test animals. After the rats were intragastrically administered Fedratinib and the compounds of the preferred embodiments of the present invention, the drug concentration in the plasma at different times was determined through the LC/MS/MS method to study the pharmacokinetic characteristics of the compounds of the present invention in rats.

Source of SD rats: Shanghai Slack Laboratory Animal Co., Ltd.
Administration: Single intragastric administration
Dosage and concentration: 25 mg/kg; 2 mg/mL
Prescription of preparations: 0.5% methylcellulose
Sampling points: 5 min, 15 min, 30 min, 1 h, 2 h, 4 h, 8 h, and 24 h.
Standard curve and preparation and processing of quality control samples:

Stock solution was diluted with 50% acetonitrile/water solution to obtain standard working solutions of 0.04, 0.10, 0.20, 0.40, 1.00, 2.00, 4.00 μg/mL, and quality control working solutions of 0.10, 1.00, 3.00 μg/mL. 2.50 μL of standard curve working solutions and quality control working solutions were added to 47.5 μL of blank rat plasma, respectively, to obtain standard curve solutions having analyte concentrations of 2.00, 5.00, 10.00, 20.00, 50.00, 100.00, 200.00 ng/mL and quality control samples having concentrations of 5.00, 50.00, and 150.00 ng/mL. 200 μL of acetonitrile (containing 5 ng/mL of the internal standard loratadine) was added. After vortexing for 3 minutes, the solutions were centrifuged at 15000 rpm at 4° C. for 15 minutes. 100 μL of the supernatant was taken for LC-MS/MS analysis. WinNonlin® 8.0 was used to calculate the experimental results.

The pharmacokinetic parameters of the preferred compounds of the present invention are shown in Table 4.

TABLE 4

Pharmacokinetic parameters of preferred compounds

Pharmacokinetic experiment (25 mg/kg)

| Compound | Time to peak $T_{max}$ (h) | Blood concentration $C_{max}$ (ng/mL) | Curve area $AUC_{last}$ (h*ng/mL) | Half life $t_{1/2}$ (h) |
| --- | --- | --- | --- | --- |
| Fedratinib | 1.5 | 579 | 559 | 4.0 |
| I-1 | 1.0 | 998 | 798 | 5.8 |
| I-2 | 1.5 | 1024 | 839 | 6.0 |
| I-3 | 1.5 | 1231 | 903 | 5.9 |
| I-4 | 1.5 | 1098 | 807 | 6.2 |
| I-5 | 1.5 | 1123 | 812 | 6.1 |
| I-13 | 2.0 | 979 | 955 | 5.5 |
| I-14 | 1.5 | 1230 | 900 | 6.9 |
| I-15 | 1.5 | 1240 | 934 | 6.8 |
| I-19 | 1.5 | 1120 | 935 | 6.2 |
| I-20 | 2.0 | 1032 | 912 | 6.3 |

Conclusion: The compounds of the examples of the present invention exhibited good pharmacokinetic properties and had superior pharmacokinetic benefits over Fedratinib.

Test Example 4: Acute Toxicity Test of the Compounds of the Present Invention 7 compounds of the present invention (I-1, 1-2, 1-4, 1-13, 1-15, 1-19, and 1-20) and Fedratinib (positive control drug) were chosen for acute toxicity experiments.

(1) Experimental Protocol a) After oral administration of Fedratinib and compounds of the present invention such as I-1 to ICR mice, the toxicity symptoms and death of mice were observed. The acute toxicity of Fedratinib and compounds of the present invention such as I-1 was compared.

b) Solvent preparation: An appropriate amount of Tween-80 was weighed and diluted with deionized water to obtain 5% (g/v) Tween-80.
c) Dosage preparation: The predetermined test samples were weighed and added with 5% Tween 80 solution to obtain suspensions having the concentration of 6.25, 12.50, 25.00, 50.00, 75.00 and 100.00 mg/mL (equivalent to 125, 250, 500, 1000, 1500, 2000 mg/kg, respectively).
d) Administration route: The test samples and the controls (0.5% Tween-80) were administrated orally.
e) Dosing frequency: single administration, fasting overnight before administration.
f) Dosing volume: 20 mL/kg.

Observation of General Symptoms

On the day of administration, observations were made approximately 0.5, 1, 2, 4, and 6 hours after the first administration. During day 2 to day 6 of the observation period, observations were made twice a day, once in the morning and once in the afternoon.

Observations included but not limited to: general conditions, behavioral activities, gait and posture, eyes, mouth, nose, gastrointestinal tract, skin hair and urogenital tract.

(2) Statistical Analysis

Weight data were expressed as mean±standard deviation. Levene's test and one-way analysis of variance were used for comparison between groups. If there was a difference, Dunnet t test was then used.

(3) Experimental Results 7 compounds of the present invention and Fedratinib (positive control drug) were chosen for acute toxicity experiments as described above. The experimental results are shown in Table 5.

In the MTD test, the animal's tolerance to drugs was observed. The maximum tolerated dose refers to the dose administered when the animal was dying.

TABLE 5

Acute toxicity test results of single oral administration of Fedratinib such as I-1 and compounds

| test substance | MTD (mg/kg) |
| --- | --- |
| Fedratinib | 250 |
| I-1 | >2000 |
| I-2 | 1500 |
| I-4 | 1000 |
| I-13 | 1500 |
| I-15 | >2000 |
| I-19 | 1500 |
| I-20 | >2000 |

Note:
MTD represents maximum tolerated dose.

Results: The MTD (maximum tolerated dose) of the compounds I-1, 1-15, and 1-20 of the present invention in the above-mentioned test substances were all greater than 2000 mg/kg, and the acute toxicity was far lower than that of Fedratinib. The MTD of compounds 1-2, 1-4, I-13, and 1-19 are all greater than or equal to 1000 mg/kg, and the safety is better than that of Fedratinib.

The above descriptions are only preferred embodiments of the present invention, and are not intended to limit the present invention. Any modification, equivalent replacement, improvement, etc. made within the spirit and principle of the present invention shall be included in the protection scope of the present invention.

What is claimed is:

1. A selective dihydropyrrolopyrimidine JAK2 inhibitor of formula I or a pharmaceutically acceptable salt thereof:

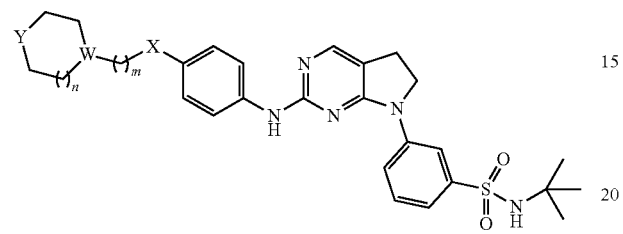

I wherein
X is O or does not exist;
Y is O, S, SO$_2$ or NR;
W is N or CH;
R is hydrogen, C$_{1-6}$ alkyl, C$_{2-6}$ alkenyl, C$_{2-6}$ alkynyl, C$_{1-6}$ alkoxy or C$_{1-6}$ carbonyl;
m is 0, 1, 2, 3, 4, 5 or 6; and
n is 0, 1 or 2.

2. The selective dihydropyrrolopyrimidine JAK2 inhibitor of formula I or pharmaceutically acceptable salt thereof according to claim 1, wherein
X is O or does not exist;
Y is O, S, SO$_2$ or NR;
W is N or CH;
R is hydrogen or C$_{1-4}$ alkyl;
m is 0, 1, 2 or 3; and
n is 0 or 1.

3. The selective dihydropyrrolopyrimidine JAK2 inhibitor of formula I or pharmaceutically acceptable salt thereof according to claim 1, wherein
X is O or does not exist;
Y is O, S, SO$_2$ or NR;
W is N or CH;
R is hydrogen or methyl;
m is 0, 1 or 2; and
n is 0 or 1.

4. The selective dihydropyrrolopyrimidine JAK2 inhibitor of formula I or pharmaceutically acceptable salt thereof according to claim 1, being a compound selected from the group consisting of:

| Compound | Structural formula |
|---|---|
| I-2 | |
| I-3 | |
| I-4 | |

-continued

| Compound | Structural formula |
|---|---|
| I-6 | |
| I-7 | |
| I-8 | |
| I-9 | |
| I-10 | |
| I-11 | |

-continued
| Compound | Structural formula |
|---|---|
| I-12 | 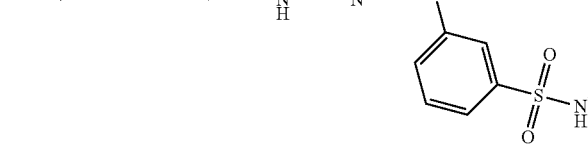 |
| I-13 | 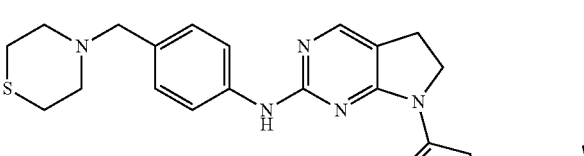 |
| I-14 | 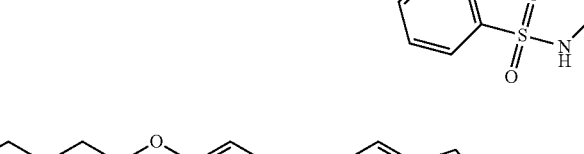 |
| I-15 | 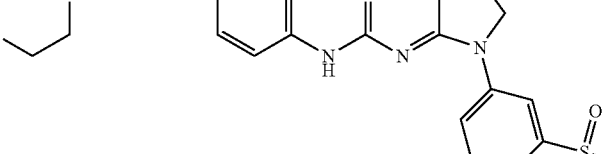 |
| I-16 |  |

-continued
| Compound | Structural formula |
|---|---|
| I-17 | 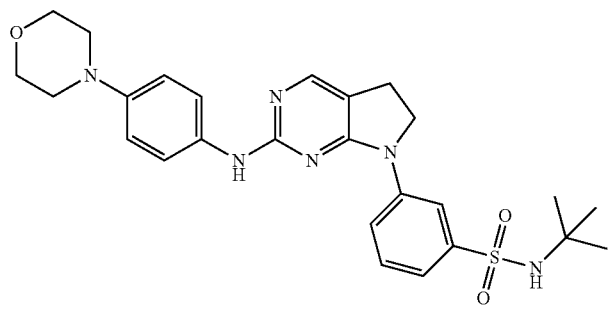 [SMILES: CC(C)(C)NS(=O)(=O)c1cccc(N2CCc3cnc(Nc4ccc(N5CCOCC5)cc4)nc32)c1] |
| I-19 | 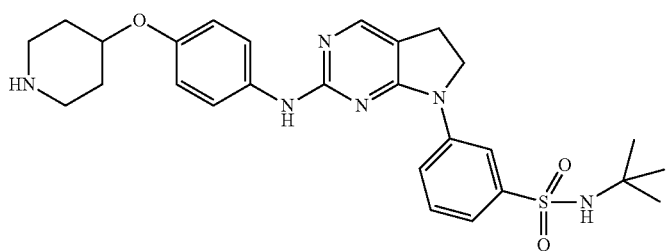 [SMILES: CC(C)(C)NS(=O)(=O)c1cccc(N2CCc3cnc(Nc4ccc(OC5CCNCC5)cc4)nc32)c1] |
| I-20 | 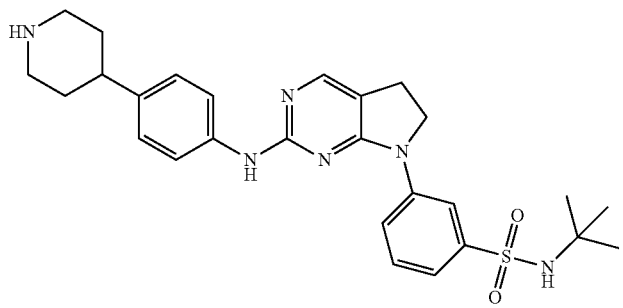
and |
| I-21 | 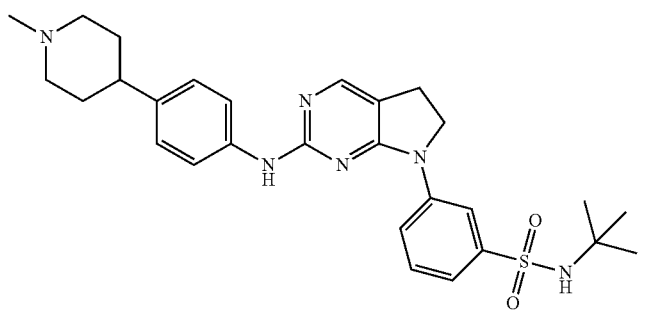 [SMILES: CN1CCC(c2ccc(Nc3ncc4c(n3)N(c3cccc(S(=O)(=O)NC(C)(C)C)c3)CC4)cc2)CC1] |

5. A method for preparing the selective dihydropyrrolo-pyrimidine JAK2 inhibitor of formula I or pharmaceutically acceptable salt thereof according to claim 1, comprising the steps of:
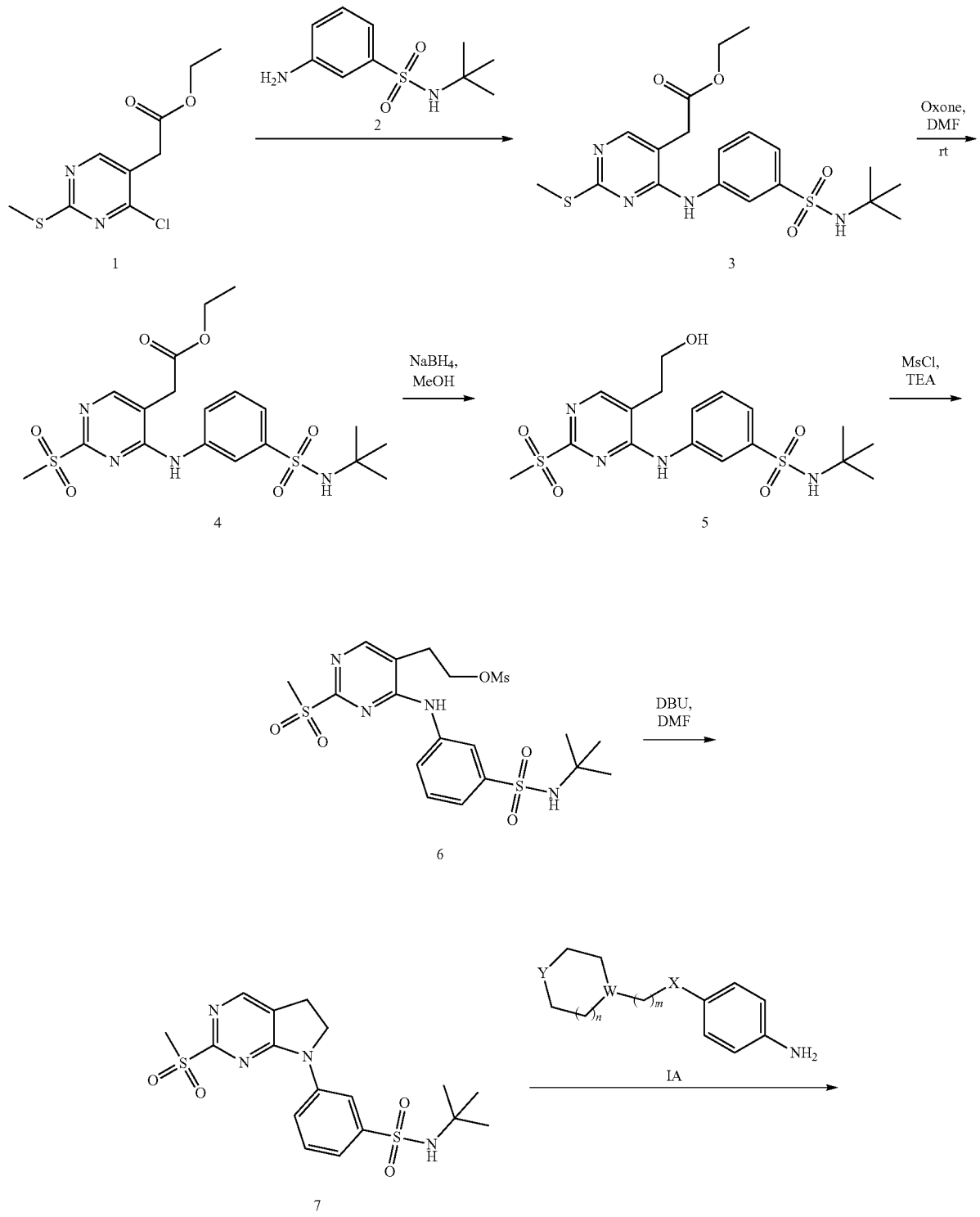

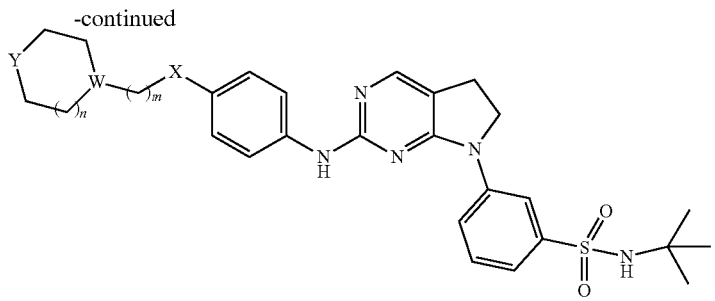

I (1) subjecting compounds 1 and 2 to a condensation reaction to give a compound 3;
(2) oxidizing the compound 3 with potassium hydrogen persulfate to give a compound 4;
(3) reducing the compound 4 with sodium borohydride to give a compound 5;
(4) activating the hydroxyl group of the compound 5 with methanesulfonyl chloride, followed by a cyclization reaction, to give a compound 7; and
(5) subjecting the compound 7 and a compound of formula IA to a condensation reaction to give the final product of formula I, wherein
X is O or does not exist;
Y is O, S, $SO_2$ or NR;
W is N or CH;
R is hydrogen, $C_{1-6}$ alkyl, $C_{2-6}$ alkenyl, $C_{2-6}$ alkynyl, $C_{1-6}$ alkoxy or $C_{1-6}$ carbonyl;
m is 0, 1, 2, 3, 4, 5 or 6; and
n is 0, 1 or 2.

6. A method for treating JAK-related diseases, wherein the method comprises administering to a patient having the JAK-related disease Use of the selective dihydropyrrolopyrimidine JAK2 inhibitor of formula I or pharmaceutically acceptable salt thereof according to claim 1.

7. The method according to claim 6, wherein the JAK-related disease is selected from the group consisting of organ-graft rejection, lupus, multiple sclerosis, rheumatoid arthritis, juvenile arthritis, psoriasis, ulcerative colitis, Crohn's disease, autoimmune thyroid disease, itching, atopic dermatitis, asthma, rhinitis, hepatitis B, hepatitis C, varicella-zoster virus, diabetes mellitus type I and diabetic complications, Alzheimer's disease, xerophthalmia, myelofibrosis, thrombocytosis, polycythemia, leukemia, multiple myeloma, prostate cancer, kidney cancer, liver cancer, pancreatic cancer, stomach cancer, breast cancer, lung cancer, head and neck cancer, thyroid cancer, glioblastoma, melanoma, lymphoma, leukemia and cutaneous T-cell lymphoma.

8. A composition comprising a therapeutically effective amount of the selective dihydropyrrolopyrimidine JAK2 inhibitor of formula I or pharmaceutically acceptable salt thereof according to claim 1 and a pharmaceutically acceptable carrier.

9. A selective dihydropyrrolopyrimidine JAK2 inhibitor or pharmaceutically acceptable salt thereof, being a compound selected from the group below consisting of:

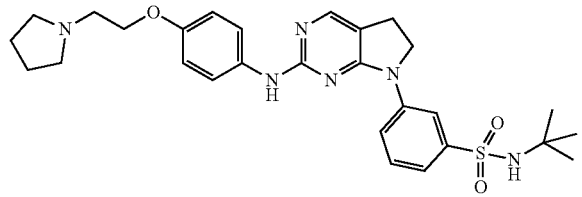

I-1

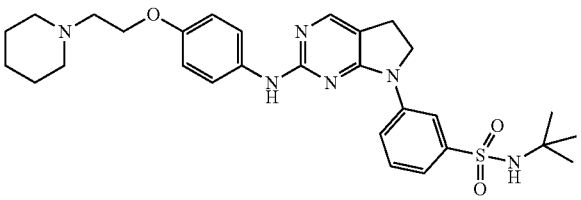

I-5

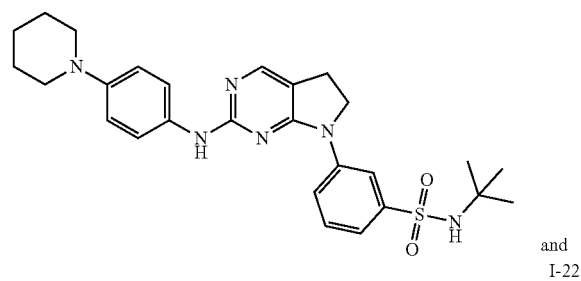

I-18

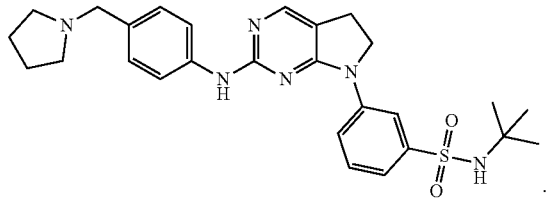

I-22 and

10. A method for treating JAK-related diseases, wherein the method comprises administering to a patient having the JAK-related disease the selective dihydropyrrolopyrimidine JAK2 inhibitor or pharmaceutically acceptable salt thereof according to claim 9.

11. The method according to claim 10, wherein the JAK-related disease is selected from the group consisting of organ-graft rejection, lupus, multiple sclerosis, rheumatoid arthritis, juvenile arthritis, psoriasis, ulcerative colitis, Crohn's disease, autoimmune thyroid disease, itching, atopic dermatitis, asthma, rhinitis, hepatitis B, hepatitis C, varicella-zoster virus, diabetes mellitus type I and diabetic complications, Alzheimer's disease, xerophthalmia, myelofibrosis, thrombocytosis, polycythemia, leukemia, multiple myeloma, prostate cancer, kidney cancer, liver cancer, pancreatic cancer, stomach cancer, breast cancer, lung cancer, head and neck cancer, thyroid cancer, glioblastoma, melanoma, lymphoma, leukemia and cutaneous T-cell lymphoma.

12. A composition comprising a therapeutically effective amount of the selective dihydropyrrolopyrimidine JAK2 inhibitor or pharmaceutically acceptable salt thereof according to claim 9 and a pharmaceutically acceptable carrier.

* * * * *